(12) United States Patent
Kamei et al.

(10) Patent No.: US 9,023,969 B2
(45) Date of Patent: *May 5, 2015

(54) POWDER SURFACE-TREATED WITH AN ORGANOPOLYSILOXANE HAVING CARBOXYL GROUPS, A DISPERSION OF THE SAME, AND A COSMETIC COMPRISING THE SAME

(75) Inventors: Masanao Kamei, Annaka (JP); Ryuichi Inaba, Ichikawa (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 455 days.

This patent is subject to a terminal disclaimer.

(21) Appl. No.: 12/417,154

(22) Filed: Apr. 2, 2009

(65) Prior Publication Data

US 2009/0252774 A1 Oct. 8, 2009

(30) Foreign Application Priority Data

Apr. 3, 2008 (JP) .................................. 2008-097568
Mar. 27, 2009 (JP) .................................. 2009-079283

(51) Int. Cl.

| | |
|---|---|
| *C08G 77/04* | (2006.01) |
| *C08G 77/14* | (2006.01) |
| *A61K 8/06* | (2006.01) |
| *A61K 8/25* | (2006.01) |
| *A61K 8/26* | (2006.01) |
| *A61K 8/27* | (2006.01) |
| *A61K 8/29* | (2006.01) |
| *A61K 8/894* | (2006.01) |
| *A61K 8/897* | (2006.01) |
| *A61Q 1/02* | (2006.01) |
| *A61Q 1/06* | (2006.01) |
| *A61Q 1/10* | (2006.01) |
| *A61Q 5/00* | (2006.01) |
| *A61Q 5/12* | (2006.01) |
| *A61Q 15/00* | (2006.01) |
| *A61Q 17/04* | (2006.01) |

(Continued)

(52) U.S. Cl.
CPC ............... *C08G 77/14* (2013.01); *A61K 8/066* (2013.01); *A61K 8/25* (2013.01); *A61K 8/26* (2013.01); *A61K 8/27* (2013.01); *A61K 8/29* (2013.01); *A61K 8/894* (2013.01); *A61K 8/897* (2013.01); *A61Q 1/02* (2013.01); *A61Q 1/06* (2013.01); *A61Q 1/10* (2013.01); *A61Q 5/00* (2013.01); *A61Q 5/12* (2013.01); *A61Q 15/00* (2013.01); *A61Q 17/04* (2013.01); *A61Q 19/00* (2013.01); *C08G 77/38* (2013.01); *C08K 9/06* (2013.01)

(58) Field of Classification Search
USPC ........................................... 528/26; 424/401
See application file for complete search history.

(56) References Cited

U.S. PATENT DOCUMENTS

| | | |
|---|---|---|
| 4,431,789 A | 2/1984 | Okazaki et al. |
| 4,486,405 A | 12/1984 | Klein |

(Continued)

FOREIGN PATENT DOCUMENTS

| | | |
|---|---|---|
| AT | 503652 A4 | 12/2007 |
| DE | 198 22 618 C1 | 2/2000 |

(Continued)

OTHER PUBLICATIONS

The European Search Report for EP Appl. No. 09 25 1036.1, dated Jun. 17, 2009.

(Continued)

*Primary Examiner* — Renee Claytor
*Assistant Examiner* — Shobha Kantamneni
(74) *Attorney, Agent, or Firm* — Birch, Stewart, Kolasch & Birch, LLP

(57) ABSTRACT

A powder surface-treated with an organopolysiloxane represented by the following average compositional formula (1):

$$R^1_a R^2_b R^3_c SiO_{(4-a-b-c)/2} \quad (1)$$

wherein $R^1$ is selected from the group consisting of C1-30 alkyl, C1-30 fluoroalkyl, C6-30 aryl, and C6-30 aralkyl groups, $R^2$ is a group represented by the following formula (2), provided that $R^2$ is bonded to at least one terminal end of the organopolysiloxane when c equals 0, $$-R^4-CR^6COOR^5 \atop | \atop CR^6R^7COOR^5 \quad (2)$$

$R^3$ is a group represented by the following formula (3):

$$-Q-(SiO)_k-SiR^8_{3-h} \atop R^8 \quad R^2_h \quad (3)$$

wherein $R^2$ is as defined above, each $R^8$ is, independently, selected from the group consisting of C1-30 alkyl, C1-30 fluoroalkyl, C6-30 aryl, and C6-30 aralkyl groups, Q is $C_dH_{2d}$ or an oxygen atom, wherein d is an integer of from 1 to 5, k is an integer of from 0 to 500, and h is an integer of from 0 to 3,
a is a number of from 1.5 to 2.5,
b is a number of from 0.001 to 1.5, and
c is a number of from 0 to 1.5.

13 Claims, No Drawings

(51) Int. Cl.
*A61Q 19/00* (2006.01)
*C08G 77/38* (2006.01)
*C08K 9/06* (2006.01)

(56) References Cited

U.S. PATENT DOCUMENTS

| | | |
|---|---|---|
| 4,598,135 A | 7/1986 | Buese |
| 4,876,152 A | 10/1989 | Kang |
| 4,935,332 A | 6/1990 | Lauke et al. |
| 5,063,052 A | 11/1991 | Grollier et al. |
| 5,385,999 A | 1/1995 | D'Anvers et al. |
| 5,470,910 A | 11/1995 | Spanhel et al. |
| 5,536,304 A | 7/1996 | Coppens et al. |
| 6,103,222 A | 8/2000 | Goldsworthy et al. |
| 6,117,435 A | 9/2000 | Painter et al. |
| 6,184,329 B1 | 2/2001 | Jost et al. |
| 6,491,981 B1 | 12/2002 | Guichard et al. |
| 6,592,854 B1 | 7/2003 | Dupuis |
| 7,163,674 B2 * | 1/2007 | Majeti et al. .......... 424/70.1 |
| 7,645,397 B2 * | 1/2010 | Parce et al. .......... 252/301.36 |
| 2002/0028899 A1 | 3/2002 | Breunig et al. |
| 2003/0211057 A1 | 11/2003 | Majeti et al. |
| 2003/0212231 A1 | 11/2003 | Olier |
| 2003/0212232 A1 | 11/2003 | Majeti et al. |
| 2004/0091439 A1 | 5/2004 | Kamei et al. |
| 2004/0156809 A1 * | 8/2004 | Ono et al. .......... 424/70.12 |
| 2005/0250904 A1 | 11/2005 | Okawa et al. |
| 2010/0234323 A1 | 9/2010 | Holzl et al. |

FOREIGN PATENT DOCUMENTS

| | | |
|---|---|---|
| EP | 1 213 316 A2 | 6/2002 |
| EP | 1 489 128 A1 | 12/2004 |
| JP | 9-59125 A | 3/1997 |
| JP | 2002-114849 A | 4/2002 |
| JP | 2002-518420 A | 6/2002 |
| JP | 2003-146832 A | 5/2003 |
| JP | 2004-231607 A | 8/2004 |
| JP | 2005-97151 A | 4/2005 |
| JP | 2005-132786 A | 5/2005 |
| JP | 2007-22972 A | 2/2007 |
| JP | 2009-538953 A | 11/2009 |
| WO | WO 96/32432 A1 | 10/1996 |
| WO | WO-03/094871 A1 | 11/2003 |
| WO | WO-03/095530 A1 | 11/2003 |

OTHER PUBLICATIONS

European Search Report dated Jun. 9, 2009 for EP Application No. 09 25 0776.3.
Notice of Allowance dated Jun. 15, 2011 for corresponding U.S. Appl. No. 12/417,403.
Office Action dated Feb. 23, 2011 for corresponding U.S. Appl. No. 12/417,403.
Office Action dated Jul. 8, 2011 for corresponding U.S. Appl. No. 12/408,393.
Office Action dated Oct. 1, 2013 for Japanese Application No. 2009-079283 with English Translation.
Japanese Office Action for corresponding Application No. 2009-079283 dated Feb. 12, 2013 (with English translation).

* cited by examiner

POWDER SURFACE-TREATED WITH AN ORGANOPOLYSILOXANE HAVING CARBOXYL GROUPS, A DISPERSION OF THE SAME, AND A COSMETIC COMPRISING THE SAME

CROSS REFERENCES

This application claims benefits of Japanese Patent Application No. 2008-097568 filed on Apr. 3, 2008, and No. 2009-79283 filed on Mar. 27, 2009, the contents of which are hereby incorporated by reference.

FIELD OF THE INVENTION

The present invention relates to a surface-treated powder, specifically a powder which is surface-treated with an organopolysiloxane having carboxyl groups and has excellent dispersivity in unctuous agents and water-resistance. The present invention also relates to a dispersion of the powder and a cosmetic comprising the powder.

BACKGROUND OF THE INVENTION

As an organopolysiloxane which has a carboxyl group and is used as a surface treatment agent, a carboxyl group-containing organopolysiloxane is known from JP 9-59125A. Powder treated with the organopolysiloxane, however, does not have satisfactory water-resistance.

The following organopolysiloxane having two carboxyl groups is known from JP 2002-114849A.

$$-R^1-N\begin{matrix} \overset{O}{\overset{\|}{C}}-R^2-\overset{O}{\overset{\|}{C}}-OM \\ \\ R^3-X-\overset{O}{\overset{\|}{C}}-R^4-\overset{O}{\overset{\|}{C}}-OM \end{matrix}$$

wherein X is —O— or —NH—, M is a hydrogen atom, metal, ammonium or the like. Powder treated with the organopolysiloxane, however, does not have satisfactory water-resistance, which is presumably due to the presence of many polar groups, i.e., amide and carbonyl groups, in the organopolysiloxane.

The organopolysiloxane described in WO 03/095530 A1 and WO 03/094871 A1 does not have amide or carbonyl groups.

$$-B-CR\begin{matrix} E-C(O)OM \\ \\ C(O)OM \end{matrix}$$

However, powder surface-treated with the organopolysiloxane does not satisfactorily disperse in an unctuous agent such as isododecane.

SUMMARY OF THE INVENTION

An object of the present invention is to provide powder which is excellent in water-resistance and dispersivity in an unctuous agent.

The present invention is a powder surface-treated with an organopolysiloxane represented by the following average compositional formula (1):

$$R^1_a R^2_b R^3_c SiO_{(4-a-b-c)/2} \quad (1)$$

wherein $R^1$ is selected from the group consisting of C1-30 alkyl, C1-30 fluoroalkyl, C6-30 aryl, and C6-30 aralkyl groups, $R^2$ is a group represented by the following formula (2), provided that $R^2$ is bonded to at least one terminal end of the organopolysiloxane when c equals 0, $$-R^4-CR^6COOR^5 \quad (2)$$
$$\qquad\quad |$$
$$\qquad\quad CR^6R^7COOR^5$$

wherein $R^4$ is a C2-20 divalent hydrocarbon group which has an oxygen atom or no oxygen atom, each $R^5$ is, independently, a hydrogen atom, a monovalent cation, or a C1-10 alkyl groups provided that at least one of $R^5$'s is a hydrogen atom or a monovalent cation, each $R^6$ is, independently, a hydrogen atom or a C1-6 alkyl group, and $R^7$ is a hydrogen atom or a C1-6 alkyl group, $R^3$ is a group represented by the following formula (3):

$$-Q-(\underset{\underset{R^8}{|}}{\overset{\overset{R^8}{|}}{Si}}O)_k-\underset{\underset{R^2_h}{|}}{\overset{}{Si}}R^8_{3-h} \quad (3)$$

wherein $R^2$ is as defined above, each $R^8$ is, independently, selected from the group consisting of C1-30 alkyl, C1-30 fluoroalkyl, C6-30 aryl, and C6-30 aralkyl groups, Q is $C_dH_{2d}$ or an oxygen atom, wherein d is an integer of from 1 to 5, k is an integer of from 0 to 500, and h is an integer of from 0 to 3, a is a number of from 1.5 to 2.5, b is a number of from 0.001 to 1.5, and c is a number of from 0 to 1.5.

The aforesaid powder of the present invention is surface-treated with a surface treatment agent having a highly reactive carboxyl groups to be excellent in water-resistance and dispersivity in an unctuous agent. A dispersion of the powder is stable, and a cosmetic comprising the powder has good usability and stability with time.

DETAILED DESCRIPTION OF THE PREFERRED EMBODIMENTS

In the following, the present invention is explained in the order of I. Powder treatment agent, II. Powder and treatment method of the powder, III. Powder dispersion, and IV. Cosmetic comprising the treated powder.

<I. Powder Treatment Agent>

The present invention is a powder surface-treated with an organopolysiloxane represented by the following average compositional formula (1):

$$R^1_a R^2_b R^3_c SiO_{(4-a-b-c)/2} \quad (1)$$

In the compositional formula (1), $R^1$ is a group selected from the group consisting of C1-30 alkyl, C1-30 fluoroalkyl, C6-30 aryl and C6-30 aralkyl groups. Examples of $R^1$ include alkyl groups such as methyl, ethyl, propyl, butyl, pentyl, hexyl, heptyl, octyl, nonyl, decyl, and stearyl groups; alicyclic groups such as cyclopentyl and cyclohexyl groups: aryl groups such as phenyl, and tolyl groups; aralkyl groups such as benzyl, and phenetyl groups; and fluoroalkyl groups such as trifluoropropyl and heptadecafluorodecyl groups. Among these, $C_{1-15}$ alkyl and phenyl groups are preferred, and a methyl group is more preferred.

$R^2$ is represented by the following formula (2):

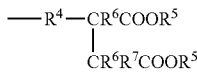
(2)

wherein a $R^4$ is a C2-20, preferably C2-12, divalent hydrocarbon group, which may have an oxygen atom. Examples of $R^4$ include alkylene groups such as ethylene, propylene, hexamethylene, decamethylene, and hexadecamethylene groups; and oxyalkylene groups such as oxyethylene and oxypropylene groups, among which ethylene and propylene groups are preferred.

$R^2$ is bonded to at least one end of the organopolysiloxane. In the organopolysiloxane having $R^3$, $R^2$ may be bonded to an

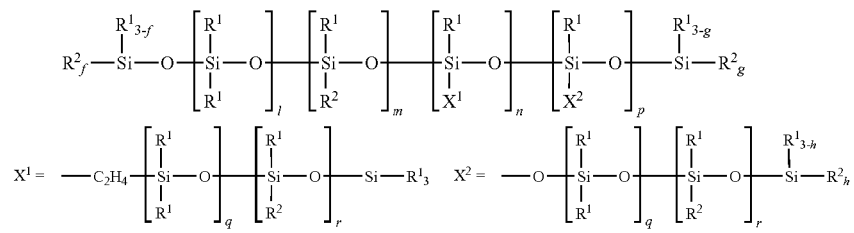

end of the $R^3$ and may be bonded to a site other than the ends of the organopolysiloxane main chain. Preferably, $R^2$ is bonded to an end of the organopolysiloxane main chain, and more preferably there is only one $R^2$ that is bonded to an end of the organopolysiloxane main chain. It is considered, though not to limit the present invention, the terminal $R^2$ allows fast reaction with a surface of substrate such as powder, and the rest part of the organopolysiloxane achieves good affinity with an unctuous agent.

Each of $R^5$ is, independently, a hydrogen atom, a monovalent cation or a C1-10 alkyl group, provided that at least one of $R^5$'s is a hydrogen atom or a monovalent cation. Examples of the monovalent cation include ions of alkali metals such as lithium, sodium, and potassium; ammonium and alkylammonium. Examples of the alkyl group include methyl, ethyl, propyl, and isopropyl groups. Preferably, $R^5$ is a hydrogen atom, a sodium ion or a potassium ion.

$R^6$ is each, independently, a hydrogen atom or a C1-6 alkyl group, and preferably a hydrogen atom or a methyl group. $R^7$ is a hydrogen atom or a C1-6 alkyl group, and preferably a hydrogen atom or a methyl group.

In the formula (1), $R^3$ is a group represented by the following formula (3):

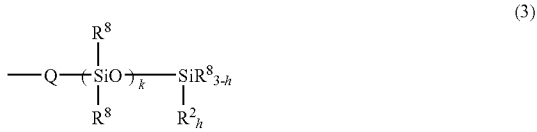
(3)

wherein each $R^8$ is, independently, selected from the group consisting of C1-30 alkyl, C1-30 fluoroalkyl, C6-30 aryl, and C6-30 aralkyl groups. Examples of $R^8$ include those aforementioned for $R^1$ among which a methyl group is preferred. Q is $C_dH_{2d}$, wherein d is an integer of from 1 to 5, preferably from 2 to 4, or an oxygen atom, preferably $C_2H_4$. k is an integer of from 0 to 500, preferably from 1 to 100, and more preferably from 5 to 60 h is an integer of from 0 to 3, preferably 0.

In the formula (1), a is a number of from 1.5 to 2.5, preferably from 1.8 to 2.3, b is a number of from 0.001 to 1.5, preferably from 0.01 to 0.5, and more preferably from 0.01 to 0.09, and c is a number of from 0 to 1.5, preferably from 0 to 0.6, more preferably from 0 to 0.3. An organopolysiloxane with b being smaller than the aforementioned lower limit may not have sufficient reactivity and adsorption capability of carboxyl groups. On the other hand, an organopolysiloxane with b and c being greater than 1.5 tends to have a viscosity too high to handle with ease.

An exemplary organopolysiloxane of the present organopolysiloxane is represented by the following formula:

wherein Q and h are as defined above, l is an integer of from 0 to 500, m is an integer of from 0 to 50, n is an integer of from 0 to 50, p is an integer of from 0 to 50, q is an integer of from 0 to 500, r is an integer of from 0 to 50, f and g are integers of from 0 to 3, provided that 1≤f+g. Preferably, l is an integer of from 5 to 60, m is an integer of from 0 to 10, n is an integer of from 1 to 10, p is an integer of from 0 to 10, q is an integer of from 1 to 100, r is an integer of from 0 to 5, f, g and h are 0 or 1, provided that f+g+h is at least one, 5≤l+m≤550. Preferably, l+m ranges from 10 to 300, and q+r ranges from 1 to 100, more preferably from 5 to 60.

The above powder treatment agent can be prepared by a method comprising the following steps:

(1) subjecting an organohydrogenpolysiloxane having hydrogen atoms at the sites where $R^2$ and $R^3$ are to be bonded and an acid anhydride compound represented by the following formula (4) to an addition reaction,

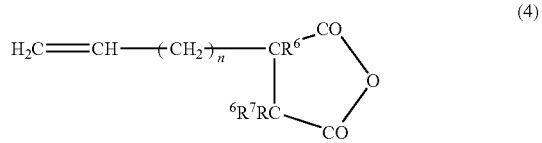
(4)

wherein each $R^6$ is, independently, a hydrogen atom or a C1-6 alkyl group, $R^7$ is a hydrogen atom or a C1-6 alkyl group, and n is an integer of from 0 to 18, and (2) subjecting a product obtained in the step (1) to a ring-opening reaction in the presence of water.

With an additional step (3) reacting a carboxylic acid obtained in the step (2) with an organic or inorganic base, an organopolysiloxane with its proton being replaced with a monovalent cation can be prepared.

The organohydrogenpolysiloxane used in the step (1) can be linear or branched. The branched organohydrogenpolysiloxane is the one having a network structure with a $(R^1SiO_{3/2})$ unit and/or a $(SiO_{4/2})$ unit. A SiH bond is located on at least one end of a main chain of the organohydrogenpolysiloxane. It may be located at an end of a side-chain, if there is a side-chain. It bond may be located at a site other than the ends when there is a silicone side-chain, but preferably at an end.

In the formula (4), $R^6$ and $R^7$ are as defined above and n is an integer of from 0 to 18, preferably from 0 to 10. Examples of the acid anhydride compound include succinic acid anhydride and derivatives thereof such as vinyl succinic acid anhydride, allyl succinic acid anhydride, allyl-2-methylsuccinic acid anhydride, allyl-2,3-dimethyl succinic acid anhydride, and allyl-2-ethyl succinic acid anhydride. Preferably, allyl succinic acid anhydride is used.

The addition reaction in the step (1) is preferably performed in the presence of a platinum or rhodium catalyst. Examples of preferred catalyst include chloroplatinic acid, chloroplatinic acid modified with an alcohol, and a complex of chloroplatinic acid with a vinylsiloxane. An amount of the catalyst to be used may be a catalytically effective amount, i.e., a catalytic amount, which is usually at most 50 ppm, particularly at most 20 ppm, as platinum or rhodium metal. The reaction may be performed in an organic solvent as needed. Examples of the organic solvent include aliphatic alcohols such as methanol, ethanol, 2-propanol and butanol; aromatic hydrocarbons such as toluene and xylene; aliphatic or alicyclic hydrocarbons such as n-pentane, n-hexane, and cyclohexane; and halogenated hydrocarbons such as dichloromethane, chloroform, and carbon tetrachloride. Reaction conditions for the addition reaction are not limited to particular ones. Preferably, the reaction is performed under reflux for 1 to 10 hours.

In the step (1), $R^3$ with Q being $C_dH_{2d}$ and h being 0 can be introduced to the organopolysiloxane by subjecting an organopolysiloxane represented by the following formula (5) having an unsaturated group at an end to an addition reaction in parallel with the addition reaction of the aforesaid acid anhydride.

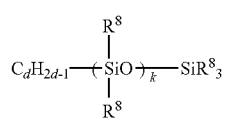

(5)

In the formula (5), $R^8$, k, and d are as defined above. $R^3$ with Q being an oxygen atom can be prepared by forming a siloxane backbone through an equilibration reaction and then reacting the organohydrogenpolysiloxane thus obtained with the aforementioned acid anhydride of the formula (4).

The ring-opening reaction in the step (2) is performed by adding water to reactants according to a conventional method. An amount of water to be added is at least an equivalent molar amount, preferably from two- to five-fold molar amounts, of the acid anhydride group. The reaction may be performed in an organic solvent as needed. Examples of the organic solvent include those listed for the step (1). The reaction conditions for the ring-opening reaction are not limited to the particular ones. Preferably, the reaction is performed at a temperature of from room temperature to a reflux temperature for 1 to 10 hours. A basic catalyst such as an amine or ammonium in an amount of from 1 to 1,000 ppm may be added to promote the ring-opening reaction.

In the ring-opening reaction, use of a C1-10 alcohol or its metal alcoholate in place of water produces an organopolysiloxane with $R^5$ being C1-10 alkyl group in the formula (2).

Examples of the base used in the step (3) include metal hydroxides such as sodium hydroxide and potassium hydroxide, and amines such as ammonia water and trialkylamine. The metal hydroxides can be added in the form of an aqueous solution or alcoholic solution.

The organopolysiloxane surface treatment agent has a carboxyl equivalent (g/mol) of from 100 to 50000, preferably from 500 to 10000, more preferably from 500 to 5000. For good handling property, the organopolysiloxane preferably has a viscosity of from 10 to 1,000,000 mm²/sec, more preferably from 10 to 100,000 mm²/sec. Further, the organopolysiloxane preferably has a weight average molecular weight reduced to polystyrene of from 200 to 100,000, more preferably from 200 to 50,000. If the weight average molecular weight exceeds 100,000, viscosity becomes too high to handle with ease. On the other hand, an organopolysiloxane having a weight average molecular weight below 200 has too little siloxane units to make the best of the siloxane units.

<II. Powder and Treatment Method>

In the present invention, any powder which is commonly used in cosmetics may be used, regardless of the shape such as spherical, spindle forms, acicular, and plate-like; particle size such as fume size, fine particles and pigment grade; and particle structure such as porous and non-porous. Examples of the powder include inorganic powder, organic powder, metal salt powder of surface active agent, colored pigments, pearl pigments, metallic powder pigments, and natural colors.

Examples of the powder of inorganic substance include powder of titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectoliter, zeolite, ceramics powder, calcium secondary phosphate, alumina, aluminum hydroxide, boron nitride, silica, and sylated silica.

Examples of the organic powder include polyamide powder such as Nylon-6 an Nylon-12 powder, polyacrylic acid/acrylate powder, polyester powder, polyethylene powder, polypropylene powder, polystyrene powder, polyurethane powder, benzoguanamine powder, polymethylbenzoguanamine powder, tetrafluoroethylene powder, polymethylmethacrylate powder, cellulose powder, silk powder, crosslinked dimethylsilicone, polymethylsilsesquioxane, spherical silicone gum coated with polymethylsilsesquioxane particles, lipophylized silica powder, natural polymers such as, starch powder, silk powder, and microcrystalline fiber powder and lauroyl lysine powder.

Examples of the powder of metal salt of surface active agent (metal soaps) include powder of zinc stearate, aluminum stearate, calcium stearate, magnesium stearate, zinc myristate, magnesium myristate, zinc cetyl phosphate, calcium cetyl phosphate, and zinc/sodium cetyl phosphate, zinc palmitate, aluminum palmitate, and zing laurate.

Examples of colored pigments include inorganic red pigments such as pigments composed of iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, lakes of tar pigments, lakes of natural dyes, and composite powders of these powder with a synthetic resin.

Examples of the pearl pigments include powder of titanium oxide-coated mica, titanium oxide-coated mica, bismuth oxychloride, titanium oxide-coated bismuth oxychloride, titanium oxide-coated talc, fish scales, and titanium oxide-coated colored mica; and metallic powder pigments such as aluminum powder, copper powder and stainless powder.

Examples of the tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and natural pigments such as carminic acid, laccaic acid, carthamin, brazilin, and crocin.

The powder which scatters ultraviolet light can be used such as titanium oxide fine particles, iron-containing titanium oxide fine particles, zinc oxide fine particles, serium oxide fine particles and composite of the powder.

For the cosmetic of the present invention, powder of zinc oxide, titanium oxide, mica, sericite, talc, and kaolin are preferred.

For treating the powder, the powder treatment agent in the present invention is used in an amount of from 0.1 to 30, preferably from 0.5 to 10, parts by weight per 100 parts by weight of the powder.

Powder treatment can be performed by known methods, for example, the following ones:

1. Mixing powder with a surface treatment agent and treating the powder with a milling apparatus such as a ball mill, bead mill, jet mill or high-pressure homogenizer;

2. Dissolving or dispersing a surface treatment agent in a solvent, in which powder is dispersed to allow the surface treatment agent to adsorb on the powder surface, and then heat-drying and baking; and 3. Dispersing powder in an aqueous solvent, to which a surface treatment agent or its aqueous emulsion is added to allow the surface treatment agent to adsorb on the powder surface, and then heat-drying and baking.

As the solvent, a hydrocarbon solvent such as toluene can be used. As the aqueous solvent, a mixture of water and an alcohol can be used. In these solvent, the aforementioned amount of the powder treatment agent in the present invention is dissolved, dispersed or emulsified. The baking is performed at a temperature of from 100 to 180° C. for about 1 to 5 hours, which may be varied depending on the solvent used.

<III. Powder Dispersion>

By dispersing the surface-treated powder in an unctuous agent, a stable dispersion can be obtained. Examples of the unctuous agent include hydrocarbon, ester, and silicone unctuous agents. Examples of the hydrocarbon unctuous agent include ozokerite, α-olefin oligomer, light isoparaffin, isododecane, isohexadecane, light liquid paraffin, squalane, synthetic squalane, plant-origin squalane, squalene, and ceresin, among which isododecane, and isohexadecane are preferred.

Examples of the ester unctuous agent include diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, isononyl isononanate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl. Examples of glyceride oils include acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristyl isostearate, among which isocetyl isostearate, cetyl octanoate, and isononyl isononanate are preferred.

Examples of the silicone unctuous agent include linear or branched organopolysiloxanes having low to high viscosities such as dimethylpolysiloxane, tristrimethylsiloxymethylsilane, caprylyl methicone, phenyltrimethicone, tetrakistrimethylsiloxysilane, methylphenylpolysiloxane, methylhexylpolysiloxane, methylhydrogenpolysiloxane, and copolymers of dimethylsiloxane and methylphenylsiloxane; cyclic organopolysiloxanes such as octamethylcyclotetrasiloxane, decamethylcyclopentasiloxane, dodecamethylcyclohexasiloxane, and tetramethyl-tetrahydrogencyclotetrasiloxane; amino-modified oganopolysiloxanes, pyrrolidonyl-modified oganopolysiloxanes, pyrrolidonyl/carboxyl-modified organopolysiloxanes; silicone rubbers such as gummy dimethylpolysiloxanes having high polymerization degrees, gummy amino-modified organopolysiloxanes, and gummy dimethylsiloxane/methylphenylsiloxane copolymers and solutions of silicone rubber in cyclic organopolysiloxane; trimethylsiloxysilicate, and solutions of trimethylsiloxysilicate in cyclic siloxane, higher alkoxy-modified silicones such as stearoxysilicone, higher fatty acid-modified silicones, alkyl-modified silicones, long chain alkyl-modified silicones, amino acid-modified silicones, fluorinated silicones, silicone resins and solutions of silicone resins, among which cyclic organopolysiloxanes such as octamethylcyclotetrasiloxane, decamethylcyclopentasiloxane, dodecamethylcyclohexasiloxane, tetramethyl-tetrahydrogencyclotetrasiloxane, and tetramethyltetraphenylcyclotetrasiloxane are preferred.

In preparation of the dispersion, 1 to 70 parts by weight, preferably 2 to 60 parts by weight of the powder is dispersed in 30 to 99 parts by weight, preferably from 40 to 98 parts by weight, of an unctuous agent, with a known means such as a bead mill.

<IV. Cosmetic Comprising the Treated Powder>

The aforementioned powder can be used for various kinds of cosmetics, particularly, those externally applied to the skin or hair such as skincare products, makeup products, hair products, antiperspirant products, and ultraviolet light protective products. The powder can be incorporated in a cosmetic in an amount of from 0.1 to 99 wt % relative to a total weight of the cosmetic according to type and form of the cosmetic. The powder may be incorporated in the cosmetic in the form of dispersion prepared in advance.

The cosmetic of the present invention may comprise various components commonly incorporated in cosmetics such as (A) an unctuous agent, (B) water, (C) a compound having an alcoholic hydroxyl group, (D) a water-soluble or water-swellable polymer (E) a powder and/or a colorant other than the powder of the present invention, (F) a surfactant, (G) a silicone resin, and (H) a composition consisting of a crosslinked organopolysiloxane and an unctuous agent which is liquid at room temperature, (I) a silicone wax, and other additives.

The unctuous agent (A) may be solid, semi-solid or liquid. Example of the unctuous agent include natural plant or animal unctuous agent and semi-synthetic unctuous agent, hydrocarbon unctuous agent, higher alcohol unctuous agent, ester unctuous agent, silicone unctuous agent, and fluorinated unctuous agent. The hydrocarbon, ester, and silicone unctuous agents described above can be used.

Examples of the natural plant or animal oils and semi-synthetic oils include avocado oil, linseed oil, almond oil, Ibota wax, perilla oil, olive oil, cacao butter, kapok wax, kaya oil, carnauba wax, Glycyrrhiza oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methylester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolate, hexyl laurate, POE lanolin alcohol ether, POE lanolin alcohol acetate, polyethylene glycol lanolate, POE hydrogenated lanolin alcohol ether, and egg yolk oil, wherein POE represents polyoxyethylene.

Examples of the higher alcohol include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (cerakyl alcohol).

The unctuous agent (A) can be incorporated in the cosmetic in an amount of from 1 to 98 wt % relative to a total weight of the cosmetic according to form of the cosmetic.

Water (B) may be incorporated in the cosmetic in an amount of from 1 to 95 weight % relative to a total weight of the cosmetic, which amount can be adjusted depending on form of the cosmetic.

Examples of the compound having an alcoholic hydroxyl group (C) include lower alcohols such as ethanol, and isopropanol; sugar alcohols such as sorbitol, and maltose; sterols such as cholesterol, sitosterol, phytosterol, and lanosterol; and polyalcohols such as butylene glycol, propylene glycol, dibutylene glycol, and pentylene glycol. A conent of the compound having an alcoholic hydroxyl group can be varied from 0.1 to 98 wt % relative to a total weight of the cosmetic.

Examples of (D) the water-soluble or water-swellable polymer include gum Arabic, tragacanth gum, arabinogalactan, locust bean gum (carob gum), guar gum, karaya gum, carrageenan, pectin, agar-agar, quince seed (i.e., marmelo), starch from rice, corn, potato or wheat, algae colloid, and trant gum; bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether, polyvinylpyrrolidone, and carboxyvinyl polymer; polyoxyethylene polymers such as polyethylene glycol; polyoxyethylene/polyoxypropylene copolymers; acrylic polymers such as sodium polyacrylate, polyethyl acrylate, and polyacrylamide; polyethyleneimine; cationic polymers; and inorganic thickening agents such as, bentonite, aluminum magnesium silicate, montmorillonite, videlite, nontronite, saponite, hectorite, and silicic anhydride. Film forming polymers such as polyvinyl alcohol and polyvinylpyrrollidone are also included. An amount of the water-soluble or water-swellable polymer (D) in the cosmetic ranges preferably from 0.1 to 25 wt % relative to a total amount of the cosmetic.

As the powder and/or colorants (E) other than the powder of the present invention, the aforementioned powder as it is and composite thereof can be used. The powder and/or colorants may be treated with a silicone oil, fluorine compound, or surfactant. A linear or branched organopolysiloxane having a hydrolysable silyl group or SiH bond, a linear or branched organopolysiloxane having a long alkyl chain and hydrolysable silyl group or SiH bond, a linear or branched organopolysiloxane having a polyoxyalkylene moiety and hydrolysable silyl group or SiH bond, an acryl silicone copolymer having a hydrolysable silyl group or SiH bond may be used. Two or more of the treatment agents may be employed. The powder and/or colorants is incorporated in the cosmetic in such an amount that it does not adversely affect the present invention.

As the surfactant (F), an anionic, cationic, nonionic or amphoteric surfactant can be used.

Examples of the anionic surfactant include fatty acid soaps, such as sodium stearate and triethanolamine palmitate, alkylether carboxylic acids and salts thereof, salts of condensates of amino acids with fatty acids, alkyl sulfonate salts, alkenesulfonates, sulfonates of fatty acid esters, fatty acid amide sulfonates, sulfonate salts of the formalin condensates, salts of alkyl sulfates, salts of secondary higher alcohol sulfates, salts of alkyl/allyl ether sulfates, salts of fatty acid ester sulfates, salts of fatty acid alkylolamide sulfates, and salts of Turkey Red oil sulfate, alkyl phosphate salts, ether phosphate salts, alkylallylether phosphate salts, amide phosphate salts, and N-acylamino surfactants.

Examples of the cationic surfactants include amine salts such as alkylamine salts, amine salts of polyamine and amino alcohol fatty acid derivatives, alkyl quaternary ammonium salts, aromatic quaternary ammonium salts, pyridinium salts and imidazolium salts.

Examples of the nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, linear or branched polyoxyalkylene-modified organopolysiloxane, linear or branched polyoxyalkylene/alkyl-comodified organopolysiloxane, linear or branched polyglycerin-modified organopolysiloxane, polyglycerin/alkyl-comodified modified organopolysiloxane alkanolamide, sugar ethers, and sugar amides.

Examples of the amphoteric surfactant include betaine, aminocarboxylates, imidazoline derivatives, and amide amine type.

Among these surfactants, preferred are a linear or branched organopolysiloxane having a polyoxyethylene group, linear or branched organopolysiloxane having a polyglyceryl group, linear or branched organopolysiloxane having a polyoxyethylene and C6-20 alkly groups, and linear or branched organopolysiloxane having a polyglyceryl and C6-20 alkly groups. In these surfactants, a content of hydrophilic polyoxyalkylene or polyglyceryl group preferably ranges from 10 to 70 wt % of the surfactant molecule. A content of the surfactant in the cosmetic preferably ranges from 0.1 to 20 mass %, more preferably from 0.2 to 10 mass %, based on total mass of the cosmetic.

Preferably, the silicone resin (G) is an acrylic silicone such as an acryl/silicone graft copolymer and acryl/silicone block copolymer. Preferably, use may be made of an acryl/silicone resin having at least one group selected from the group consisting of pyrrolidonyl, long-chain alkyl, polyoxyalkylene, and fluoroalkyl groups and anionic groups such as a carboxyl group.

Another preferred silicone resin include silicone network resins composed of $R^1_3SiO_{0.5}$ and $SiO_2$ units, those composed of $R^1_3SiO_{0.5}$, $R^1_2SiO$, and $SiO_2$ units, those composed of $R^1_3SiO_{0.5}$ and $R^1SiO_{1.5}$ units, those composed of $R^1_3SiO_{0.5}$, $R^1_2SiO$, and $R^1SiO_{1.5}$ units, and those composed of $R^1_3SiO_{0.5}$, $R^1_2SiO$, $R^1SiO_{1.5}$, and $SiO_2$ units. The silicone network compound may have at least one group selected from the group consisting of pyrrolidonyl, long-chain alkyl, polyoxyalkylene, fluoroalkyl, and amino groups. The aclyic silicone resin or the silicone resin is incorporated in the cosmetic preferably in an amount of from 0.1 to 20 wt %, more preferably from 1 to 10 wt %.

Preferably, in the composition consisting of a crosslinked organopolysiloxane and unctuous agent which is liquid at room temperature (H), the crosslinked organopolysiloxane is swelled with a liquid unctuous agent in a larger amount than the organopolysiloxane itself. As the unctuous agent, the component (A) such as a silicone, hydrocarbon, ester, natural animal and plant, semi-synthetic, and fluorinated unctuous agents can be used, for example, a silicone unctuous agent having a low viscosity of from 0.65 mm²/sec to 10.0 mm²/sec (25° C.); hydrocarbon oils such as liquid paraffin, squalane, isododecane, and isohexadecane; glycerides such as trioctanoin; esters such as isotridecyl isononanate, N-acyl glutamate, and lauroyl sarcosinate; and natural animal and plant unctuous agent such as macadamin nuts oil.

Preferred crosslinked organopolysiloxane is a reaction product of an organopolysiloxane having at least two vinylic reaction sites per molecule and an organohydrogenpolysiloxane having a Si—H bond. Examples of organopolysiloxane having at least two vinylic reaction sites per molecule include an organopolysiloxane having at least two vinyl groups, a polyoxyalkylene having at least two ally groups, a polyglycerin having at least two ally groups, and α,ω-alkenyldiene.

The crosslinked organopolysiloxane may have at least one group selected from polyoxyalkylene, polygryceryl, alkyl, alkenyl, aryl and fluoroalkyl groups. The composition consisting of a crosslinked organopolysiloxane and unctuous agent is incorporated in the cosmetic preferably in an amount of from 0.1 to 80 wt %, more preferably from 1 to 50 wt %.

The silicone wax (I) is produced by addition-reacting an olefin wax with an organohydrogenpolysiloxane having at least one SiH bond per molecule. Preferred olefin wax is polymers of C2-12 α-olefin such as ethylene, propylene, 1-butene, 1-hexene, 4-methyl-1-pentene; polymers a diene such as butadiene, isoprene, 1,4-hexadiene, vinylnorbornene, ethylidene norbornene, dicylopentadiene. The organohydrogenpolysiloxane may be linear or branched.

In the cosmetic of the present invention, other components that are commonly used in cosmetics can be incorporated in an amount not to adversely affect the cosmetic. Examples of the components include oil-soluble gelling agents, clay minerals modified with organic compounds, resins, antiperspirants, ultraviolet absorbents, ultraviolet absorbing and scattering agents, moisture retention agents, antiseptics, antimicrobial agents, perfumes, salts, antioxidants, pH regulators, a chelating agents, refreshing agents, an anti-inflammatory agent, skin beautifying components, such as skin whitener, cell activator, rough dry skin improver, blood circulation promoter, skin astringent and anti-seborrheic agent, vitamins, amino acids, nucleic acids, hormones, clathrate compounds, and hair setting agents.

Examples of the oil-soluble gelling agent include metal soaps, such as aluminum stearate, magnesium stearate and zinc myristate; amino acid derivatives, such as N-lauroyl-L-glutamic acid and α,γ-di-n-butylamine; dextrin fatty acid esters, such as dextrin palmitic acid ester, dextrin stearic acid ester and dextrin 2-ethylhexaminic acid palmitic acid ester; inulin fatty acid esters such as fructooligostearate; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of the antiperspirant include aluminum chlorohydrate, aluminum chloride, aluminum sesquichlorohydrate, zirconium hydroxychloride, aluminum zirconium hydroxychloride, and aluminum zirconium glycine complex.

Examples of the UV absorbents include UV absorbents of benzoic acid type such as p-aminobenzoic acid; those of anthranilic acid type such as methyl anthranilate; those of salicylic acid type such as methyl salicylate, octyl salicylate, and trimethylcyclohexyl salicylate; those of succinic acid type such as octyl p-methoxysuccinate; those of benzophenone type, such as 2,4-dihydroxybenzophenone; those of urocanic acid type, such as ethyl urocanate; those of dibenzoylmethane type such as 4-t-butyl-4'-methoxydibenzoylmethane; and phenylbenzoimidazol sulfonic acid. Examples of the ultraviolet scattering agents include fine powder of titanium oxide, fine powder of iron-containing titanium oxide, fine powder of zinc oxide, fine powder of cerium oxide, and a mixture of these powders. Dispersion of these ultraviolet absorbing or scattering agents in an oil can be used, too.

Examples of moisture retention agents include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, and polyoxypropylene methylglycoside.

Examples of the antiseptics include alkyl paraoxybenzoates, benzoic acid, sodium benzoate, sorbic acid, potassium sorbate, and phenoxyethanol may be used. For the antibacterial agents, benzoic acid, salicylic acid, carbolic acid, sorbic acid, paraoxybenzoic acid alkyl esters, parachloromethacresol, hexachlorophene, benzalkonium chloride, chlorohexydine chloride, trichlorocarbanilide and phenoxyethanol.

Examples of the salts include inorganic salts, organic acid salts, salts of amine and salts of amino acids. Examples of the inorganic salts include sodium, potassium, magnesium, calcium, aluminum, zirconium, or zinc salt of inorganic acid such as hydrochloric acid, sulfuric acid, carbonate acid, and nitric acid. Examples of the salts of organic acid include salts of organic acid such as acetic acid, dehydroacetic acid, citric acid, malic acid, succinic acid, ascorbic acid, and stearic acid. Examples of the salts of amine or amino acid include salt of triethanol amine and salt of glutamic acid. Other examples are salt of hyaluronic acid, chondroitin sulfate, aluminum/zirconium/glycine chelate, and salts produced by acid-alkaline neutralization reaction in the cosmetic.

Examples of the antioxidants include tocopherol, butylhydroxyanisole, dibutylhydroxytoluene and phytic acid; examples of the pH regulators include lactic acid, citric acid, glycolic acid, succinic acid, tartaric acid, dl-malic acid, potassium carbonate, sodium hydrogen carbonate and ammonium hydrogen carbonate; examples of the chelating agents include alanine, sodium ethylenediamine tetraacetate, sodium polyphosphate, sodium metaphosphate and phosphoric acid; examples of the refrigerants include L-menthol and camphor; and examples of the anti-inflammatory agents include allantoin, glycyrrhizin and salts thereof, glycyrrhetinic acid and stearyl glycyrrhetinate, tranexamic acid and azulene.

Examples of the skin-beautifying components include whitening agents, such as placenta extract, arbutin, glutathione and Yukinoshita extract; cell activators, such as royal jelly, photosensitizers, cholesterol derivatives and calf blood extract; rough and dry skin improvers; blood circulation improvers, such as nonylic acid vanillyl amide, benzyl nicotinate, beta-butoxyethyl nicotinate, capsaicin, zingerone, cantharis tincture, ichtammol, caffeine, tannic acid, alpha-borneol, tocopheryl nicotinate, inositol hexanicotinate, cyclandelate, cinnarizine, tolazoline, acetyl choline, verapamil, cepharanthin and gamma-oryzanol; skin astringents, such as zinc oxide and tannic acid; and anti-seborrheic agents, such as sulfur and thianthol.

Examples of the vitamins include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as alpha-tocopherol, beta-tocopherol, gamma-tocopherol, dl-alpha-tocopheryl acetate, dl-alpha-tocopheryl nicotinate and dl-alpha-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of the amino acids include glycine, valine, leucine, isoleucine, serine, threonine, phenylaranine, alginine, lysine, aspartic acid, glutamic acid, cystine, cysteine, methionine, and tryptophan; examples of the nucleic acids include deoxyribonucleic acid; and examples of the hormones include estradiol and ethenyl estradiol.

Examples of the polymers for hair setting include amphoteric, anionic, cationic, and nonionic polymers, such as polymers of polyvinyl pyrrolidone type such as polyvinyl pyrrolidone, vinyl pyrrolidone/vinyl acetate copolymers; acidic polymers of vinyl acetate ether type such as methyl vinyl ether/maleic acid anhydride alkyl half ester copolymer; polymers of acidic poly vinyl acetate type such as vinyl acetate/crotonic acid copolymer; acidic acrylic polymers such as (meth)acrylic acid/alkyl (meth)acrylate copolymer, (meth)acrylic acid/alkyl (meth)acrylate/alkyl acrylic amide copolymer, and amphoteric acrylic polymer such as N-methacryloylethyl-N,N-dimethylammonium alpha-N-methylcarboxybetaine/alkylmetahcrylate copolymer, hydroxypropyl (meth)acrylate/butylaminoethyl methacrylate/octyl amide of acrylic acid copolymer. Use is also made of naturally occurring polymers such as cellulose or derivatives thereof, keratin, collagen and derivatives thereof.

The cosmetic can be in various forms, for example, aqueous, oily, oil-in-water type emulsion, water-in-oil type emulsion, non-aqueous emulsion, and multi-emulsion such as W/O/W or O/W/O emulsion. The cosmetic may be in the various product forms such as lotion, milky lotion, cream, paste, gel, mousse, spray, stick, and pencil. Examples of the cosmetic include skin care cosmetic, such as face lotion, milky lotion, cream, face cleansing cream, massage materials, toilet soap and detergent, antiperspirant and deodorant; makeup cosmetic, such as face powder, foundation, rouge, eye shadow, mascara, eyeliner and lipstick; and hairdressing cosmetic, such as shampoo, rinse, treatment setting agent, antiperspirant and UV protective cosmetics, such as sunscreen milky lotion or sunscreen cream.

EXAMPLES

The present invention is explained in further detail below with reference to examples, but the present invention is in no way limited by the examples. In the following, "%" means "% by weight" unless otherwise specified.

Preparation Example 1

In a reactor, were placed 241 parts by weight of an organohydrogenpolysiloxane represented by the following formula (6):

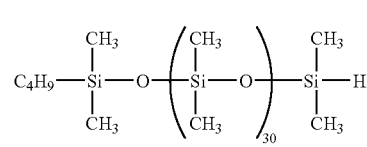

14.7 parts by weight of ally succinic acid anhydride represented by the following formula (7):

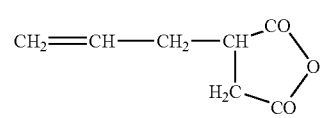

and 100 parts by weight of toluene, to which 0.1 part of a 0.5 wt % solution of chloroplatinic acid in toluene was added, and then subjected to a reaction under reflux of the solvent for 2 hours. The reaction mixture was then heated at a reduced pressure to remove the solvent, whereby a liquid having a viscosity of 82 mm$^2$/s was obtained with 98% yield. IR and 1H-NMR spectral analyses of the liquid identified it as an organopolysiloxane having acid anhydride groups represented by the following formula (8):

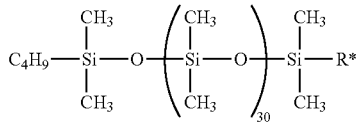

| IR | $^1$H-NMR (CDCl$_3$) |
|---|---|
| 2963 cm$^{-1}$ (C—H) | 0 ppm (s, 192H, Si—CH$_3$) |
| 1867 cm$^{-1}$ (C=O) | 0.5 ppm (t, 2H, Si—CH$_2$) |
| 1790 cm$^{-1}$ (C=O) | 0.9 ppm (t, 3H, C—CH$_3$) |
| 1260 cm$^{-1}$ (Si—CH$_3$) | 1.3 ppm (m, 4H, C—CH$_2$) |
| 1100 to 1020 cm$^{-1}$ (Si—O) | 1.4 ppm (m, 2H, C—CH$_2$) |
|  | 1.8 ppm (m, 2H, C—CH$_2$) |
|  | 2.6 ppm (m, 1H, CH—CO) |
|  | 3.1 ppm (m, 2H, CH$_2$—CO) |

To 250 parts by weight of the above organopolysiloxane having acid anhydride groups, 100 parts by weight of tetrahydrofuran and 5.4 parts by weight of water were added, which were then subjected to a reaction under reflux for 5 hours. The reaction mixture was subjected to vacuum distillation, whereby a liquid having a viscosity of 147 mm$^2$/s and a carboxyl equivalent of 1290 g/mol was obtained with 97% yield. IR and 1H-NMR spectral analyses of the liquid identified it as an organopolysiloxane having carboxyl groups represented by the following formula (9):

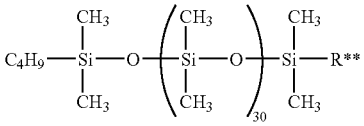

| IR | $^1$H-NMR (CDCl$_3$) |
|---|---|
| 3300 to 2500 cm$^{-1}$ (—OH) | 0 ppm (s, 189H, Si—CH$_3$) |
| 2965 cm$^{-1}$ (C—H) | 0.5 ppm (t, 6H, Si—CH$_2$) |
| 1716 cm$^{-1}$ (C=O) | 1.4 ppm (m, 6H, C—CH$_2$) |
| 1260 cm$^{-1}$ (Si—CH$_3$) | 1.8 ppm (m, 6H, C—CH$_2$) |
| 1100 to 1020 cm$^{-1}$ (Si—O) | 2.5 ppm (m, 3H, CH—CO) |
|  | 2.8 ppm (m, 6H, CH$_2$—CO) |
|  | 11.5 ppm (s, 2H, —COOH) |

Preparation Example 2

In a reactor, were placed 240 parts by weight of an organohydrogenpolysiloxane represented by the following formula (10):

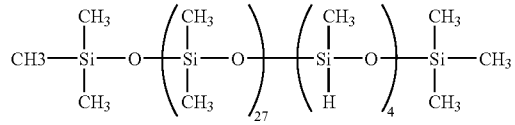

28.0 parts by weight of ally succinic acid anhydride, and 168 parts by weight of an organopolysiloxane having a vinyl group at an end represented by the following formula (11):

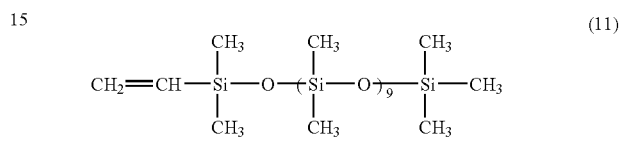

and 100 parts by weight of toluene, to which 0.1 part of a 0.5 wt % solution of chloroplatinic acid in toluene was added, and then subjected to a reaction under reflux of the solvent for 2 hours. The reaction mixture was then heated at a reduced pressure to remove the solvent, whereby a liquid having a viscosity of 110 mm$^2$/s was obtained with 98% yield. IR and $^1$H-NMR spectral analyses of the liquid identified it as an organopolysiloxane having acid anhydride groups represented by the following formula (12):

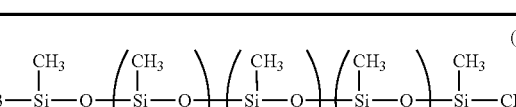

| IR | $^1$H-NMR (CDCl$_3$) |
|---|---|
| 2963 cm$^{-1}$ (C—H) | 0 ppm (s, 330H, Si—CH$_3$) |
| 1867 cm$^{-1}$ (C=O) | 0.4 ppm (m, 8H, Si—CH$_2$) |
| 1790 cm$^{-1}$ (C=O) | 0.5 ppm (t, 4H, Si—CH$_2$) |
| 1260 cm$^{-1}$ (Si—CH$_3$), | 1.4 ppm (m, 4H, C—CH$_2$) |
| 1100 to 1020 cm$^{-1}$ (Si—O) | 1.7 ppm (m, 4H, C—CH$_2$) |
|  | 2.4 ppm (m, 2H, CH—CO) |
|  | 2.8 ppm (m, 4H, CH$_2$—CO) |

To 250 parts by weight of the above organopolysiloxane having acid anhydride groups, 100 parts by weight of tetrahydrofuran and 7.2 parts by weight of water were added, which were then subjected to a reaction under reflux for 5 hours. The reaction mixture was subjected to vacuum distillation, whereby a liquid having a viscosity of 850 mm$^2$/s and a carboxyl equivalent of 1110 g/mol was obtained with 95% yield. IR and $^1$H-NMR spectral analyses of the liquid identified it as an organopolysiloxane having carboxyl groups represented by the following formula (13):

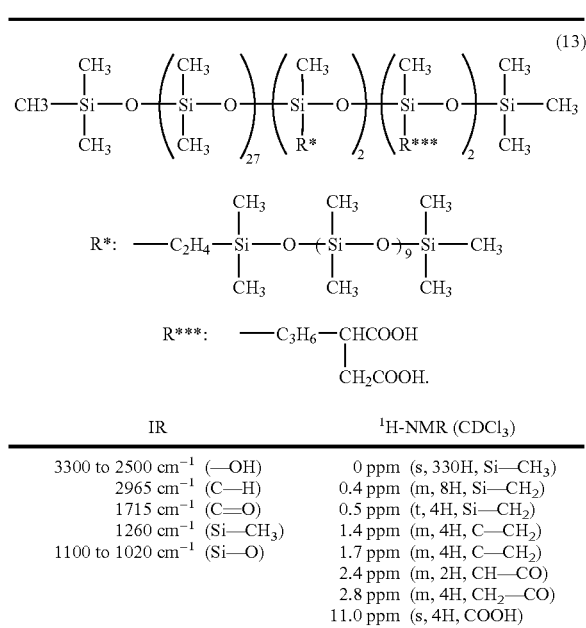

(13)

| IR | $^1$H-NMR (CDCl$_3$) |
|---|---|
| 3300 to 2500 cm$^{-1}$ (—OH) | 0 ppm (s, 330H, Si—CH$_3$) |
| 2965 cm$^{-1}$ (C—H) | 0.4 ppm (m, 8H, Si—CH$_2$) |
| 1715 cm$^{-1}$ (C=O) | 0.5 ppm (t, 4H, Si—CH$_2$) |
| 1260 cm$^{-1}$ (Si—CH$_3$) | 1.4 ppm (m, 4H, C—CH$_2$) |
| 1100 to 1020 cm$^{-1}$ (Si—O) | 1.7 ppm (m, 4H, C—CH$_2$) |
| | 2.4 ppm (m, 2H, CH—CO) |
| | 2.8 ppm (m, 4H, CH$_2$—CO) |
| | 11.0 ppm (s, 4H, COOH) |

Comparative Preparation Example 1

In a reactor, were placed 228 parts by weight of an organohydrogenpolysiloxane represented by the following formula (14);

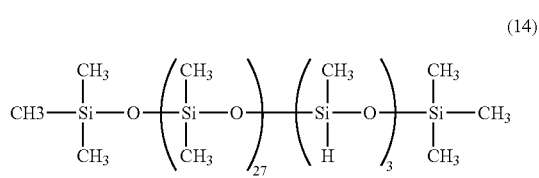

(14)

29.4 parts by weight of ally succinic acid anhydride and 100 parts by weight of toluene, to which 0.1 part of a 0.5 wt % solution of chloroplatinic acid in toluene was added, and then subjected to a reaction under reflux of the solvent for 2 hours. The reaction mixture was then heated at a reduced pressure to remove the solvent, whereby a liquid having a viscosity of 84 mm$^2$/s was obtained with 98% yield. IR and $^1$H-NMR spectral analyses of the liquid identified it as an organopolysiloxane having acid anhydride groups represented by the following formula (15):

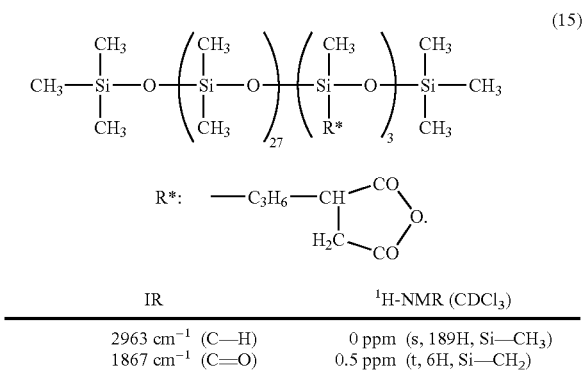

(15)

| IR | $^1$H-NMR (CDCl$_3$) |
|---|---|
| 2963 cm$^{-1}$ (C—H) | 0 ppm (s, 189H, Si—CH$_3$) |
| 1867 cm$^{-1}$ (C=O) | 0.5 ppm (t, 6H, Si—CH$_2$) |

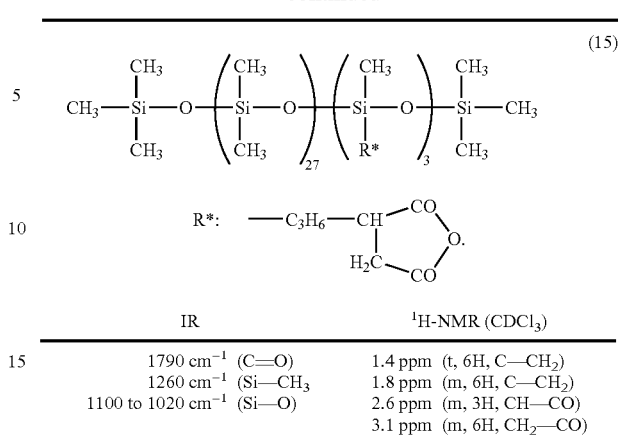

(15)

| IR | $^1$H-NMR (CDCl$_3$) |
|---|---|
| 1790 cm$^{-1}$ (C=O) | 1.4 ppm (t, 6H, C—CH$_2$) |
| 1260 cm$^{-1}$ (Si—CH$_3$) | 1.8 ppm (m, 6H, C—CH$_2$) |
| 1100 to 1020 cm$^{-1}$ (Si—O) | 2.6 ppm (m, 3H, CH—CO) |
| | 3.1 ppm (m, 6H, CH$_2$—CO) |

To 250 parts by weight of the above organopolysiloxane having acid anhydride groups, 100 parts by weight of tetrahydrofuran and 7.2 parts by weight of water were added, which were then subjected to a reaction under reflux for 5 hours. The reaction mixture was subjected to vacuum distillation, whereby a liquid having a viscosity of 8700 mm$^2$/s and a carboxyl equivalent of 435 g/mol was obtained with 97% yield. IR and $^1$H-NMR spectral analyses of the liquid identified it as an organopolysiloxane having carboxyl groups represented by the following formula (16):

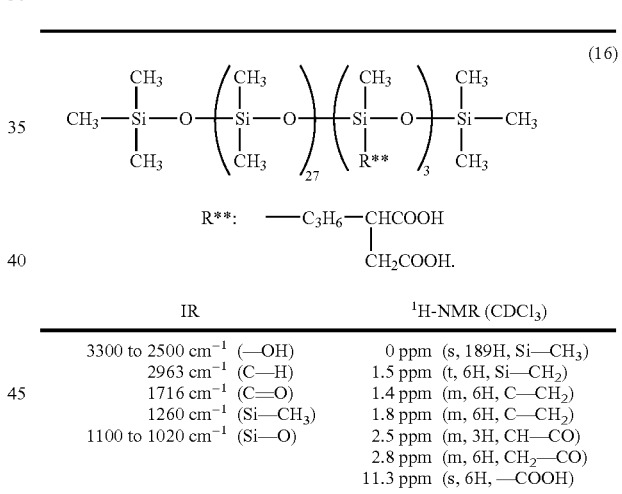

(16)

| IR | $^1$H-NMR (CDCl$_3$) |
|---|---|
| 3300 to 2500 cm$^{-1}$ (—OH) | 0 ppm (s, 189H, Si—CH$_3$) |
| 2963 cm$^{-1}$ (C—H) | 1.5 ppm (t, 6H, Si—CH$_2$) |
| 1716 cm$^{-1}$ (C=O) | 1.4 ppm (m, 6H, C—CH$_2$) |
| 1260 cm$^{-1}$ (Si—CH$_3$) | 1.8 ppm (m, 6H, C—CH$_2$) |
| 1100 to 1020 cm$^{-1}$ (Si—O) | 2.5 ppm (m, 3H, CH—CO) |
| | 2.8 ppm (m, 6H, CH$_2$—CO) |
| | 11.3 ppm (s, 6H, —COOH) |

Comparative Preparation Example 2

In a reactor, were placed 266 parts by weight of an organohydrogenpolysiloxane represented by the following formula (17):

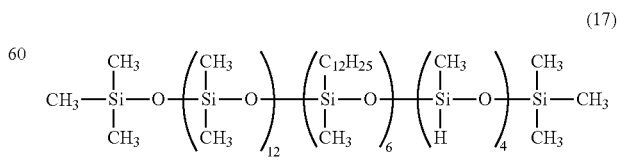

(17)

58.8 parts by weight of ally succinic acid anhydride, and 100 parts by weight of toluene, to which 0.1 part of a 0.5 wt % solution of chloroplatinic acid in toluene was added, and then subjected to a reaction under reflux of the solvent for 2 hours. The reaction mixture was then heated at a reduced pressure to remove the solvent, whereby a liquid having a viscosity of 145 mm²/s was obtained with 97% yield. IR and ¹H-NMR spectral analyses of the liquid identified it as an organopolysiloxane having acid anhydride groups represented by the following formula (18):

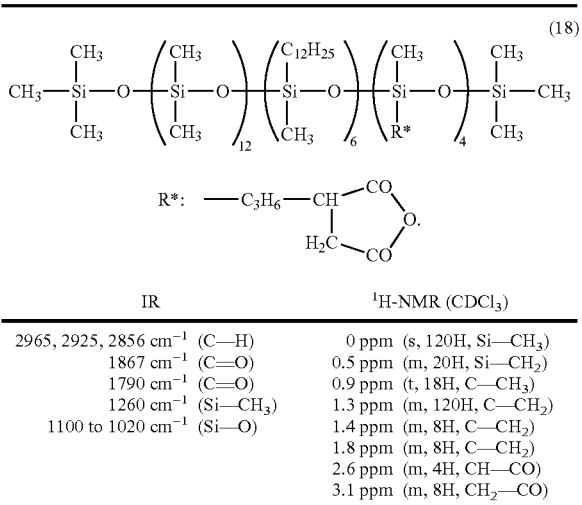

| IR | ¹H-NMR (CDCl₃) |
|---|---|
| 2965, 2925, 2856 cm⁻¹ (C—H) | 0 ppm (s, 120H, Si—CH₃) |
| 1867 cm⁻¹ (C=O) | 0.5 ppm (m, 20H, Si—CH₂) |
| 1790 cm⁻¹ (C=O) | 0.9 ppm (t, 18H, C—CH₃) |
| 1260 cm⁻¹ (Si—CH₃) | 1.3 ppm (m, 120H, C—CH₂) |
| 1100 to 1020 cm⁻¹ (Si—O) | 1.4 ppm (m, 8H, C—CH₂) |
|  | 1.8 ppm (m, 8H, C—CH₂) |
|  | 2.6 ppm (m, 4H, CH—CO) |
|  | 3.1 ppm (m, 8H, CH₂—CO) |

To 250 parts by weight of the above organopolysiloxane having acid anhydride groups, 100 parts by weight of tetrahydrofuran and 14.4 parts by weight of water were added, which were then subjected to a reaction under reflux for 5 hours. The reaction mixture was subjected to vacuum distillation, whereby a liquid having a viscosity of 9800 mm²/s and a carboxyl equivalent of 415 g/mol was obtained with 96% yield. IR and ¹H-NMR spectral analyses of the liquid identified it as an organopolysiloxane having carboxyl groups represented by the following formula (19):

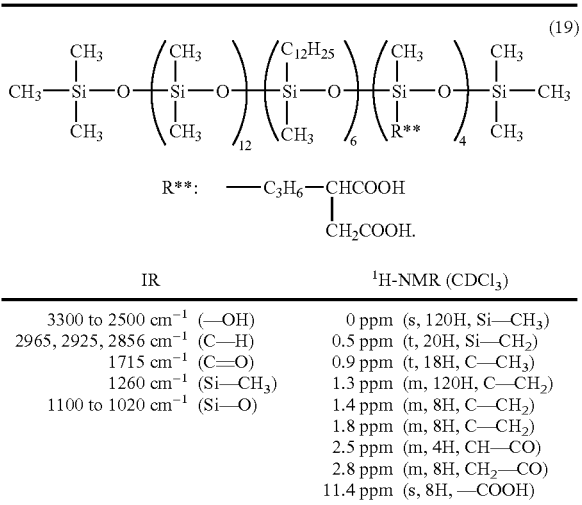

| IR | ¹H-NMR (CDCl₃) |
|---|---|
| 3300 to 2500 cm⁻¹ (—OH) | 0 ppm (s, 120H, Si—CH₃) |
| 2965, 2925, 2856 cm⁻¹ (C—H) | 0.5 ppm (t, 20H, Si—CH₂) |
| 1715 cm⁻¹ (C=O) | 0.9 ppm (t, 18H, C—CH₃) |
| 1260 cm⁻¹ (Si—CH₃) | 1.3 ppm (m, 120H, C—CH₂) |
| 1100 to 1020 cm⁻¹ (Si—O) | 1.4 ppm (m, 8H, C—CH₂) |
|  | 1.8 ppm (m, 8H, C—CH₂) |
|  | 2.5 ppm (m, 4H, CH—CO) |
|  | 2.8 ppm (m, 8H, CH₂—CO) |
|  | 11.4 ppm (s, 8H, —COOH) |

Examples 1 to 4, Comparative Examples 1 to 6

Powder of titanium dioxide or zinc oxide was treated with the organopolysiloxanes obtained in the above Preparation Examples, Comparative Preparation Examples, and a surface treatment agent (Comparative example 3), respectively, according to the formulation shown in the following Table. In a reactor, 98 parts by weight of titanium dioxide or zinc oxide powder, which had not been surface-treated and dried under vacuum, were placed, to which a solution of an organopolysiloxane dissolved in about 100 parts by weight of toluene was gradually added while stirring the powder. A temperature of the reactor was raised from room temperature to about 120° C. to remove toluene, and then to 150° C. at which temperature the powder was stirred for 3 hours. In the following table, "Ex." stands for "Example" and "Comp. Ex." for "Comparative Example."

TABLE 1

| Surface-treated powder | Powder, parts by weight | | Organopolysiloxane, parts by weight | | | | | |
|---|---|---|---|---|---|---|---|---|
|  | Titanium dioxide | Zinc oxide | Ex. 1 | Ex. 2 | Com. Ex. 1 | Comp. Ex. 2 | Comp. Ex. 3 |
| Ex. 1 | 98 |  | 2 |  |  |  |  |
| Ex. 2 | 98 |  |  | 2 |  |  |  |
| Ex. 3 |  | 98 | 2 |  |  |  |  |
| Ex. 4 |  | 98 |  | 2 |  |  |  |
| Comp. Ex. 1 | 98 |  |  |  | 2 |  |  |
| Comp. Ex. 2 | 98 |  |  |  |  | 2 |  |
| Comp. Ex. 3 | 98 |  |  |  |  |  | 2 |
| Comp. Ex. 4 |  | 98 |  |  | 2 |  |  |
| Comp. Ex. 5 |  | 98 |  |  |  | 2 |  |
| Comp. Ex. 6 |  | 98 |  |  |  |  | 2 |

Surface treatment agent used in Comparative Example 3: An organopolysiloxane having carboxyl groups represented by the following formula:

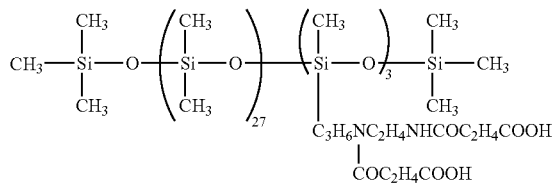

<Stability of Dispersion in an Unctuous Agent>

Dispersions of the surface-treated powders were prepared. In 50 ml of isododecane, 2.5 g of each surface-treated powder was dispersed with a bead mill. The dispersion obtained was transferred to a 50-ml test tube. The dispersion in the test tube was left standing for 2 days, and then visually observed for sedimentation of the powder. As references, dispersions of titanium dioxide powder and zinc oxide powder which had not been surface-treated were prepared in the same manner. Results are shown in the following Table 2. In the Table, values in the second column indicate a height of the uppermost powder after 2 day-standing relative to an initial height, that is, "1.0" indicates no sedimentation. A smaller value indicates a larger degree of sedimentation.

<Water-Resistance>

Water-resistance of the surface-treated powder was evaluated according to the following method: A predetermined amount of the powder was press-molded in a ca. 50 mm-Φ× 10 mm-thick disk. On the disk, a drop of a 1:1 v/v mixture of 1,3-butylene glycol and water was dropped. A time required for the drop to be absorbed in the disk was measured. A shorter time indicates worse water-resistance.

TABLE 2

| Surface-treated powder | Stability of dispersion | Water-resistance, hr |
|---|---|---|
| Example 1 | 1.0 | 5.5 |
| Example 2 | 1.0 | 6.5 |
| Example 3 | 1.0 | 5.0 |
| Example 4 | 0.9 | 5.0 |
| Comparative Example 1 | 0.7 | 5.0 |
| Comparative Example 2 | 0.8 | 5.5 |

TABLE 2-continued

| Surface-treated powder | Stability of dispersion | Water-resistance, hr |
|---|---|---|
| Comparative Example 3 | 0.5 | 3.5 |
| Comparative Example 4 | 0.8 | 4.5 |
| Comparative Example 5 | 0.7 | 5.0 |
| Comparative Example 6 | 0.6 | 3.0 |
| Non-treated titanium dioxide | 0.2 | 0 |
| Non-treated zinc oxide | 0.2 | 0 |

As shown in Table 2, powders treated with the organopolysiloxanes of the Examples showed water-resistance comparable to that of Comparative Examples, and hardly settled down, showing good dispersivity. In contrast, the powders treated with the organopolysiloxane which does not have terminal carboxyl groups or a silicone side-chain showed sedimentation. Particularly, Comparative Example 3 showed significant sedimentation.

Examples 5, 6 and Comparative Examples 7 to 9

Using the surface-treated powders, water-in-oil type sunscreen milky lotions were prepared according to the formulations shown in the following table and evaluated. In the table, "Ex." stands for "Example" and "Comp. Ex." for "Comparative Example."

| | Components | Ex. 5 | Ex. 6 | Comp. Ex. 7 | Comp. Ex. 8 | Comp. Ex. 9 |
|---|---|---|---|---|---|---|
| 1 | Crosslinked polyether-modified silicone[1] | 3.0 | ← | ← | ← | ← |
| 2 | Crosslinked dimethylpolysiloxane[2] | 2.0 | ← | ← | ← | ← |
| 3 | Branched polyether-modified silicone[3] | 1.0 | ← | ← | ← | ← |
| 4 | Dimethylpolysiloxane (6 mm$^2$/sec at 25° C.) | 5.0 | ← | ← | ← | ← |
| 5 | Decamethylcyclopentasiloxane | 36.0 | ← | ← | ← | ← |
| 6 | Isotridecyl isononanate | 4.0 | ← | ← | ← | ← |
| 7 | Titanium dioxide of Example 1 | 15.0 | ← | ← | ← | ← |
| 8 | Zinc oxide of Example 3 | 10.0 | ← | ← | ← | ← |
| 9 | Titanium dioxide of Example 2 | | 15.0 | | | |
| 10 | Zinc oxide of Example 4 | | 10.0 | | | |
| 11 | Titanium dioxide of Comparative Example 1 | | | 15.0 | | |
| 12 | Zinc oxide of Comparative Example 4 | | | 10.0 | | |
| 13 | Titanium dioxide of Comparative Example 2 | | | | 15.0 | |
| 14 | Zinc oxide of Comparative Example 5 | | | | 10.0 | |
| 15 | Titanium dioxide of Comparative Example 3 | | | | | 15.0 |
| 16 | Zinc oxide of Comparative Example 6 | | | | | 10.0 |
| 17 | Branched polyglycerin-modified silicone[4] | 4.0 | ← | ← | ← | ← |
| 18 | Silica | 0.2 | ← | ← | ← | ← |
| 19 | Dipropylene glycol | 2.0 | ← | ← | ← | ← |
| 20 | Sodium citrate | 0.2 | ← | ← | ← | ← |
| 21 | Sodium chloride | 0.5 | ← | ← | ← | ← |
| 22 | Antiseptics | q.s. | ← | ← | ← | ← |
| 23 | Perfume | q.s. | ← | ← | ← | ← |
| 24 | Purified water | 17.1 | ← | ← | ← | ← |

[1]Crosslinked polyether-modified silicone: KSG-210 from Shin-Etsu Chemical Co., Ltd.
[2]Crosslinked dimethylpolysiloxane: KSG-15 from Shin-Etsu Chemical Co., Ltd.
[3]Branched polyether-modified silicone: KF-6028 from Shin-Etsu Chemical Co., Ltd.
[4]Branched polyglycerin-modified silicone: KF-6104 from Shin-Etsu Chemical Co., Ltd.

Preparation Procedures

A: Components 7 to 17 were mixed with a part of Component 5, and a part of Component 24 and dispersed with a bead mill.

B: Components 1 to 4, the rest of Component 5, Component 6 and Component 18 were mixed.

C: Components 19 to 22 and the rest of Component 24 were mixed.

D: To the mixture prepared in the step B, the mixture prepared in the step C was added and emulsified while stirring. To the emulsion, the dispersion prepared in the step A and Component 23 were added.

The water-in-oil type sunscreen milky lotions thus obtained were evaluated by 50 women panelists. An aliquot of the milky lotion was applied to a face skin and rated in terms of affinity with the skin, spreadability on the skin, uniformity of a layer of the applied milky lotion, and resistance to sweat. Points of the rating were then averaged.

| | |
|---|---|
| 5 points | Excellent |
| 4 points | Good |
| 3 points | Average |
| 2 points | Slightly bad |
| 1 point | Bad |

| Averaged points | Overall rating |
|---|---|
| 4.5 or higher | A |
| 3.5 or higher to below 4.5 | B |
| 2.5 or higher to below 3.5 | C |
| 1.5 or higher to below 2.5 | D |
| Below 1.5 | E |

TABLE 3

| Evaluation results | Ex. 5 | Ex. 6 | Comp. Ex. 7 | Comp. Ex. 8 | Comp. Ex. 9 |
|---|---|---|---|---|---|
| Affinity with the skin | B | B | C | B | B |
| Spreadability on the skin | A | A | B | B | C |
| Uniformity of an applied lotion layer | A | B | C | C | B |
| Resistance to sweat | A | A | C | B | C |

As is found from the Table 3, the water-in-oil type milky lotions of Examples were superior to those of Comparative Examples in spreadability, affinity with the skin and sweat resistance. The milky lotions were found to be stable, for they showed no change in appearance after they were kept in closed containers at 50° C. for 3 months.

<Cosmetic>

The followings are examples of the cosmetic. Powders were treated in the same manner as in Examples 1-4, unless otherwise specified. Stability of a cosmetic with time and temperature was evaluated by change in appearance of the cosmetic after keeping it in a closed container at 50° C. for 3 months.

Example 11

Oil-In-Water Type Cream

| Components | wt % |
|---|---|
| 1. Ethyl alcohol | 17.0 |
| 2. Propylene glycol | 3.0 |
| 3. Polyether-modified silicone [1] | 0.5 |
| 4. Glyceryl trioctanoate | 2.0 |
| 5. Sericite treated with the organopolysiloxane (Preparation Example 1) | 3.0 |
| 6. Composite powder of hybrid silicone [2] | 5.0 |
| 7. Carboxyvinyl polymer (1% aqueous solution) | 20.0 |
| 8. Xanthan gum (2% aqueous solution) | 6.0 |
| 9. Triethanolamine | 0.2 |
| 10. Antiseptics | q.s. |
| 11. Perfume | q.s. |
| 12. Purified water | 60.8 |

[1] Polyether-modified silicone: KF-6011 from Shin-Etsu Chemical Co., Ltd.
[2] Composite powder of hybrid silicone: KSP-100 from Shin-Etsu Chemical Co., Ltd.

Preparation Procedures
A: Components 1 to 6 were mixed.
B: Components 7 to 12 were mixed and dissolved.
C: The mixture prepared in the step A was added to the solution prepared in the step B and emulsified.

The oil-in-water type cream thus obtained had fine texture, and was non-tacky and non-greasy. It spread smoothly and lasted long on the skin to give moisturized and refreshing feel to the skin. It was found to be stable with time and temperature.

Example 12

Body Lotion

| Components | wt % |
|---|---|
| 1. Ethyl alcohol | 17.0 |
| 2. 1,3-butylene glycol | 3.0 |
| 3. Branched polyglycerin-modified silicone [1] | 0.5 |
| 4. Glyceryl trioctanoate | 2.0 |
| 5. Talc treated with the organopolysiloxane (Preparation Example 2) | 5.0 |
| 6. Composite powder of hybrid silicone [2] | 5.0 |
| 7. Ammonium acryloyl dimethyl taurine/VPcopolymer (2% aqueous solution) | 20.0 |
| 8. Xanthan gum (2% aqueous solution) | 6.0 |
| 9. Sodium chloride (1% aqueous solution) | 1.0 |
| 10. Antiseptics | q.s. |
| 11. Perfume | q.s. |
| 12. Purified water | 40.5 |

[1] Branched polyglycerin-modified silicone: KF-6100 from Shin-Etsu Chemical Co., Ltd.
[2] Composite powder of hybrid silicone: KSP-100 from Shin-Etsu Chemical Co., Ltd.

Preparation Procedures
A: Components 1 to 6 were mixed.
B: Components 7 to 12 were mixed and dissolved.
C: The mixture prepared in the step A was added to the solution prepared in the step B.

The body lotion thus obtained spread smoothly on the skin to give non-tacky, non-greasy, moisturized and refreshing feel. It was found to be stable with time and temperature.

Example 13

Oil-In-Water Type Cream

| Components | wt % |
|---|---|
| 1. Crosslinked dimethylpolysiloxane [1] | 10.0 |
| 2. Glyceryl trioctanoate | 5.0 |
| 3. Dipropylene glycol | 7.0 |
| 4. Glycerin | 5.0 |
| 5. Methylcellulose (2% aqueous solution) [2] | 7.0 |
| 6. Polyacrylamide emulsifier [3] | 2.0 |
| 7. Polyether-modified silicone [4] | 1.0 |
| 8. Mica titanium treated with organopolysiloxane (Preparation Example 2) | 1.0 |
| 9. Antiseptics | q.s. |
| 10. Perfume | q.s. |
| 11. Purified water | 62.0 |

[1] Crosslinked dimethylpolysiloxane: KSG-16 from Shin-Etsu Chemical Co., Ltd.
[2] Methylcellulose: Metholose SM-4000 from Shin-Etsu Chemical Co., Ltd.
[3] Polyacrylamide emulsifier: Sepigel 305 from Seppic.Co.
[4] Polyether-modified silicone: KF-6043 from Shin-Etsu Chemical Co., Ltd.

Preparation Procedures
A: Components 3 to 11 were mixed.
B: Components 1 and 2 were mixed and dissolved, to which the mixture prepared in the step A was added and emulsified.

The oil-in-water type cream thus obtained had fine texture. It spread smoothly on the skin to give non-tacky, non-greasy, moisturized and refreshing feel, and lasted long on the skin. It was found to be stable with time and temperature.

Example 14

Oil-In-Water Type Cream

| Components | wt % |
| --- | --- |
| 1. Crosslinked dimethylpolysiloxane[1] | 8.0 |
| 2. Crosslinked dimethylpolysiloxane[2] | 30.0 |
| 3. Decamethylcyclopentasiloxane | 10.0 |
| 4. 1,3-butylene glycol | 3.0 |
| 5. Branched polyglycerin-modified silicone[3] | 0.6 |
| 6. Branched polyglycerin-modified silicone[4] | 0.3 |
| 7. Polyacrylamide emulsifier[5] | 0.6 |
| 8. Mica titanium treated with organopolysiloxane (Preparation Example 1) | 1.0 |
| 9. Ammonium acryloyl dimethyl taurine/VP copolymer (5% aqueous solution) | 13.0 |
| 10. Sodium chloride (1% aqueous solution) | 8.0 |
| 11. Antiseptics | q.s. |
| 12. Perfume | q.s. |
| 13. Purified water | 25.5 |

[1]Crosslinked dimethylpolysiloxane: KSG-15 from Shin-Etsu Chemical Co., Ltd.
[2]Crosslinked dimethylpolysiloxane: KSG-16 from Shin-Etsu Chemical Co., Ltd.
[3]Branched polyglycerin-modified silicone: KF-6100 from Shin-Etsu Chemical Co., Ltd.
[4]Branched polyglycerin-modified silicone: KF-6104 from Shin-Etsu Chemical Co., Ltd.
[5]Polyacrylamide emulsifier: Simulgel 600 from Seppic Co.

Preparation Procedures
A: Components 4 to 13 were mixed.
B: Components 1 to 3 were mixed.
C: To the mixture prepared in the step A, the homogeneous mixture prepared in the step B was added and emulsified.

The oil-in-water type cream thus obtained had fine texture with its inner phase having a very small particle size. It spread lightly to give non-tacky, non-greasy, moisturized and refreshing feel. It formed a beautiful layer on the skin. It was found to be stable with time and temperature.

Example 15

Water-In-Oil Type Cream

| Components | wt % |
| --- | --- |
| 1. Dimethylpolysiloxane (6 mm$^2$/sec at 25° C.) | 6.0 |
| 2. Methylphenylpolysiloxane | 4.0 |
| 3. Squalane | 5.0 |
| 4. Neopentyl glycol dioctanoate | 3.0 |
| 5. Polyether-modified silicone[1] | 3.0 |
| 6. Hydrophobic titanium oxide fine powder[2] | 2.0 |
| 7. Magnesium sulfate | 0.7 |
| 8. Glycerin | 10.0 |
| 9. Antiseptics | q.s. |
| 10. Perfume | q.s. |
| 11. Purified water | Balance |

[1]Polyether-modified silicone: KF-6017 from Shin-Etsu Chemical Co., Ltd.
[2]Hydrophobic titanium oxide fine powder was prepared as follows: Titanium dioxide fine particles having an average particle size of 0.05 μm were dispersed in water to make a 10 wt % dispersion. To the dispersion, 10 wt % solution of sodium silicate (SiO$_2$/Na$_2$O molar ratio = 0.5) in an amount of 2 wt %, as SiO$_2$, relative to titanium oxide, was added and thoroughly agitated, and then 10 wt % of aluminum sulfate solution in an amount of 7.5 wt %, as Al$_2$O$_3$, relative to titanium oxide was gradually added, whereby hydrate of silicate and alumina were deposited on titanium dioxide surface. After the deposition reaction, the dispersion was filtered, washed and then dried followed by pulverization with a jet mill. The pulverized powder was transferred to a Henschel mixer, to which 2 wt % of organopolysiloxane of Preparation Example 2 was added and mixed, and then baked at 120° C.

Preparation Procedures
A: Components 1 to 5 were heat-mixed, to which Component 6 was added and mixed.
B: Components 7 to 9 and 11 were heated and dissolved.
C: To the mixture prepared in the step A, the solution prepared in the step B was gradually added and emulsified while stirring. Then, the emulsion was cooled, to which Component 10 was added.

The water-in-oil type cream thus obtained had fine texture. It spread smoothly and lasted long on the skin to give non-tacky, non-greasy, moisturized and refreshing feel. It was found to be stable with time and temperature.

Example 16

Water-In-Oil Type Cream

| Components | wt % |
| --- | --- |
| 1. Crosslinked polyether-modified silicone[1] | 4.0 |
| 2. Crosslinked dimethylpolysiloxane[2] | 3.0 |
| 3. Branched polyether-modified silicone[3] | 1.0 |
| 4. Dimethylpolysiloxane (6 mm$^2$/sec at 25° C.) | 10.0 |
| 5. Sericite treated with organopolysiloxane (Preparation Example 1) | 2.0 |
| 6. 1,3-butylene glycol | 8.0 |
| 7. Ethyl alcohol | 5.0 |
| 8. Sodium citrate | 0.2 |
| 9. Sodium chloride | 0.5 |
| 10. Antiseptics | q.s. |
| 11. Perfume | q.s. |
| 12. Purified water | 66.3 |

[1]Crosslinked polyether-modified silicone: KSG-210 from Shin-Etsu Chemical Co., Ltd.
[2]Crosslinked dimethylpolysiloxane: KSG-15 from Shin-Etsu Chemical Co., Ltd.
[3]Branched polyether-modified silicone: KF-6028 from Shin-Etsu Chemical Co., Ltd.

Preparation Procedures
A: Components 3 to 5 were mixed, to which Components 1 and 2 were added and mixed.
B: Components 6 to 10 and 12 were mixed and dissolved.
C: To the mixture prepared in the step A, the solution prepared in the step B was added and emulsified, to which Component 11 was added.

The water-in-oil type cream thus obtained had fine texture and was non-tacky and non-greasy. It spread smoothly on the skin to give moisturized and refreshing feel. It was found to be stable with time and temperature.

Example 17

Water-In-Oil Type Makeup Base

| Components | wt % |
| --- | --- |
| 1. Crosslinked polyether-modified silicone[1] | 4.0 |
| 2. Crosslinked dimethylpolysiloxane[2] | 2.0 |
| 3. Branched polyether-modified silicone[3] | 0.5 |
| 4. Dimethylpolysiloxane (6 mm$^2$/sec at 25° C.) | 7.0 |
| 5. Dimethylpolysiloxane (20 mm$^2$/sec at 25° C.) | 2.0 |
| 6. Talc treated with organopolysiloxane (Preparation Example 1) | 2.0 |
| 7. Dispersion of titanium oxide fine particles[4] | 10.0 |
| 8. 1,3-butylene glycol | 5.0 |
| 9. Ethyl alcohol | 3.0 |
| 10. Methylcellulose (2% aqueous solution)[5] | 2.5 |
| 11. Sodium citrate | 0.2 |
| 12. Sodium chloride | 0.5 |
| 13. Antiseptics | q.s. |

-continued

| Components | wt % |
|---|---|
| 14. Perfume | q.s. |
| 15. Purified water | 61.3 |

[1] Crosslinked polyether-modified silicone: KSG-210 from Shin-Etsu Chemical Co., Ltd.
[2] Crosslinked dimethylpolysiloxane: KSG-15 from Shin-Etsu Chemical Co., Ltd.
[3] Branched polyether-modified silicone: KF-6028 from Shin-Etsu Chemical Co., Ltd.
[4] Dispersion of titanium dioxide fine particles: SPD-T5 from Shin-Etsu Chemical Co., Ltd.
[5] Methylcellulose: Metholose65-SH4000 from Shin-Etsu Chemical Co., Ltd.

Preparation Procedures

A: Components 1 to 7 were mixed.

B: Components 8 to 13 and 15 were mixed and dissolved.

C: To the mixture prepared in the step A, the solution prepared in the step B was added and emulsified, to which Component 14 was added.

The water-in-oil type makeup base thus obtained had fine texture. It spread smoothly on the skin to give non-tacky, non-greasy, moisturized and refreshing feel. It was found to be stable with time and temperature.

Example 18

Water-In-Oil Type Cream

| Components | wt % |
|---|---|
| 1. Alkyl-modified crosslinked polyether-modified silicone[1] | 4.0 |
| 2. Crosslinked alkyl-modified dimethylpolysiloxane[2] | 6.0 |
| 3. Branched alkyl/polyether-co-modified silicone[3] | 0.5 |
| 4. Liquid paraffin | 12.0 |
| 5. Neopentyl glycol dioctanoate | 5.0 |
| 6. Composite powder of hybrid silicone[4] | 1.5 |
| 7. Titanium oxide fine particles treated with organopolysiloxane (Preparation Example 1) | 2.0 |
| 8. Glycerin | 3.0 |
| 9. 1,3-butylene glycol | 7.0 |
| 10. Sodium citrate | 0.2 |
| 11. Sodium chloride | 0.5 |
| 12. Antiseptics | q.s. |
| 13. Perfume | q.s. |
| 14. Purified water | 58.3 |

[1] Alkyl-modified crosslinked polyether-modified silicone: KSG-310 from Shin-Etsu Chemical Co., Ltd.
[2] Crosslinked alkyl-modified dimethylpolysiloxane: KSG-41 from Shin-Etsu Chemical Co., Ltd.
[3] Branched alkyl/polyether-co-modified silicone: KF-6038 from Shin-Etsu Chemical Co., Ltd.
[4] Composite powder of hybrid silicone: KSP-100 from Shin-Etsu Chemical Co., Ltd.

Preparation Procedures

A: Components 1 to 7 were mixed.

B: Components 8 to 12 and 14 were mixed and dissolved.

C: To the mixture prepared in the step A, the solution prepared in the step B was added and emulsified, to which Component 13 was added.

The water-in-oil type cream thus obtained had fine texture. It spread smoothly on the skin to give non-tacky, non-greasy, moisturized and refreshing feel. It was found to be stable with time and temperature.

Example 19

Water-In-Oil Type Cream

| Components | wt % |
|---|---|
| 1. Alkyl-modified crosslinked polyether-modified silicone[1] | 6.0 |
| 2. Liquid paraffin | 13.5 |
| 3. Macadamia nut oil | 5.0 |
| 4. Branched alkyl/glycerin-co-modified silicone[2] | 0.5 |
| 5. Composite powder of hybrid silicone[3] | 3.0 |
| 6. Titanium oxide fine particles treated with organopolysiloxane (Preparation Example 1) | 2.0 |
| 7. Sodium citrate | 0.2 |
| 8. Propylene glycol | 8.0 |
| 9. Glycerin | 3.0 |
| 10. Antiseptics | q.s. |
| 11. Perfume | q.s. |
| 12. Purified water | 58.8 |

[1] Alkyl-modified crosslinked polyether-modified silicone: KSG-310 from Shin-Etsu Chemical Co., Ltd.
[2] Branched alkyl/glycerin-co-modified silicone: KF-6105 from Shin-Etsu Chemical Co., Ltd.
[3] Composite powder of hybrid silicone: KSP-100 from Shin-Etsu Chemical Co., Ltd.

Preparation Procedures

A: Components 1 to 6 were mixed.

B: Components 7 to 12 were mixed and dissolved. To the mixture prepared in the step A, the solution prepared in the step B was added and emulsified.

The water-in-oil type cream thus obtained had fine texture. It spread smoothly and lasted long on the skin to give and was non-tacky, non-greasy, moisturized and refreshing feel. It was found to be stable with time and temperature.

Example 20

Water-In-Oil Type Cream

| Components | wt % |
|---|---|
| 1. Decamethylcyclopentasiloxane | 16.0 |
| 2. Dimethylpolysiloxane (6 mm$^2$/sec at 25° C.) | 4.0 |
| 3. Polyether-modified silicone[1] | 5.0 |
| 4. POE (5)octyl dodecyl ether | 1.0 |
| 5. Polyoxyethylene sorbitan monostearate (20E.O.) | 0.5 |
| 6. Zinc oxide treated with silicic anhydride[2] | 2.0 |
| 7. Titanium oxide fine particles treated with organopolysiloxane (Preparation Example 1) | 10.0 |
| 8. Liquid paraffin | 2.0 |
| 9. Macadamia nut oil | 1.0 |
| 10. *Scutellaria* root extract[3] | 1.0 |
| 11. *Gentian* root extract[4] | 0.5 |
| 12. Ethyl alcohol | 5.0 |
| 13. 1,3-butylene glycol | 2.0 |
| 14. Antiseptics | q.s. |
| 15. Perfume | q.s. |
| 16. Purified water | Balance |

[1] Polyether-modified silicone: KF-6017 from Shin-Etsu Chemical Co., Ltd.
[2] Zinc oxide treated with silicic acid anhydride: Sunsphere SZ-5 from Asahi Glass Co., Ltd., which is composed of silica having a particle size of 0.01 to 10 μm and containing 50% of zinc oxide.
[3] *Scutellaria* root extract: Extracted with 50% aqueous solution of 1,3-butylene glycol
[4] *Gentian* root extract: Extracted with 20% aqueous solution of ethanol Preparation Procedures A: Components 6 to 9 were mixed and dispersed.

B: Components 1 to 5 were mixed, to which the dispersion prepared in the step A was added.

C: Components 10 to 14 and 16 were mixed, to which the mixture prepared in the step B was added and emulsified.

D: The emulsion prepared in the step C was cooled, to which Component 15 was added.

The water-in-oil type cream thus obtained had fine texture. It spread smoothly and lasted long on the skin to give non-tacky and non-greasy feel and gloss finish with good affinity with the skin. It was found to be stable with time and temperature.

Example 21

Eyeliner

| Components | wt % |
|---|---|
| 1. Decamethylcyclopentasiloxane | 39.0 |
| 2. Branched polyether-modified silicone[1] | 3.0 |
| 3. Organic silicone resin[2] | 15.0 |
| 4. Montmorillonite modified with dioctadecyldimethylammonium salt | 3.0 |
| 5. Iron oxide black treated with organopolysiloxane (Preparation Example 1) | 10.0 |
| 6. 1,3-butylene glycol | 5.0 |
| 7. Sodium dehydroacetate | q.s. |
| 8. Antiseptics | q.s. |
| 9. Purified water | Balance |

[1]Branched polyether-modified silicone: KF-6028 from Shin-Etsu Chemical Co., Ltd.
[2]Organic silicone resin: KF-7312J from Shin-Etsu Chemical Co., Ltd.

Preparation Procedures

A: Components 1 to 4 were mixed to which Component 5 was added and dispersed.

B: Components 6 to 9 were mixed.

C: To the dispersion prepared in the step A, the mixture prepared in the step B was gradually added and emulsified.

The eyeliner thus obtained spread smoothly on the skin and easy to apply to give non-tacky and non-greasy feel. The applied eyeliner stayed long and was resistant to sweat. The eyeliner was found to be stable with time and temperature.

Example 22

Eyeliner

| Components | wt % |
|---|---|
| 1. Decamethylcyclopentasiloxane | 22.0 |
| 2. Dimethylpolysiloxane (6 mm$^2$/sec at 25° C.) | 5.0 |
| 3. Iron oxide black treated with organopolysiloxane (Preparation Example 2) | 20.0 |
| 4. Organic silicone resin[1] | 10.0 |
| 5. Vitamin E acetate | 0.2 |
| 6. Jojoba oil | 2.0 |
| 7. Bentonite | 3.0 |
| 8. Polyether-modified silicone[2] | 2.0 |
| 9. Ethyl alcohol | 3.0 |
| 10. 1,3-butylene glycol | 5.0 |
| 11. Antiseptics | q.s. |
| 12. Purified water | Balance |

[1]Organic silicone resin: KF-7312J from Shin-Etsu Chemical Co., Ltd.
[2]Polyether-modified silicone: KF-6017 from Shin-Etsu Chemical Co., Ltd.

Preparation Procedures

A: Components 1, 2, and 4 to 8 were mixed to which Component 3 was added and dispersed.

B: Components 9 to 12 were mixed.

C: To the dispersion prepared in the step A, the mixture prepared in the step B was gradually added, emulsified and cooled.

The eyeliner thus obtained spread smoothly on the skin and easy to apply to give non-tacky and non-greasy feel. The applied eyeliner stayed long and was resistant to sweat and water. The eyeliner was found to be stable with time and temperature.

Example 23

Eyeliner

| Components | wt % |
|---|---|
| 1. Decamethylcyclopentasiloxane | 6.0 |
| 2. Dimethylpolysiloxane (6 mm$^2$/sec at 25° C.) | 5.0 |
| 3. Jojoba oil | 2.0 |
| 4. Polyether-modified silicone[1] | 1.0 |
| 5. Branched alkyl/polyether-co-modified silicone[2] | 1.0 |
| 6. Acrylic silicone resin[3] | 15.0 |
| 7. Iron oxide black treated with organopolysiloxane (Preparation Example 2) | 20.0 |
| 8. Ethyl alcohol | 5.0 |
| 9. Antiseptics | q.s. |
| 10. Purified water | Balance |

[1]Polyether-modified silicone: KF-6017 from Shin-Etsu Chemical Co., Ltd.
[2]Branched alkyl/polyether-co-modified silicone: KF-6038 from Shin-Etsu Chemical Co., Ltd.
[3]Acrylic silicone resin: KP-545 from Shin-Etsu Chemical Co., Ltd.

Preparation Procedures

A: Components 1 to 6 were mixed while warming, to which Component 7 was added and dispersed.

B: Components 8 and 9 were dissolved in Component 10 while warming.

C: To the dispersion prepared in the step A, the solution prepared in the step B was gradually added and emulsified.

The eyeliner thus obtained spread lightly on the skin to give non-greasy, non-powdery and refreshing feel. The applied eyeliner was resistant to water and sweat, and stayed long. The eyeliner was found to be stable with time and temperature.

Example 24

Powder Eyebrow

| Components | wt % |
|---|---|
| 1. Vaseline | 2.5 |
| 2. Dimethylpolysiloxane (6 mm$^2$/sec at 25° C.) | 1.5 |
| 3. Crosslinked alkyl-modified dimethylpolysiloxane[1] | 1.5 |
| 4. Glyceryl trioctanoate | 3.0 |
| 5. Mica treated with organopolysiloxane (Preparation Example 1) | 40.0 |
| 6. Talc treated with organopolysiloxane (Preparation Example 1) | Balance |
| 7. Titanium oxide (Example 1) | 10.0 |
| 8. Barium sulfate treated with organopolysiloxane (Preparation Example 1) | 15.0 |
| 9. Iron oxide treated with organopolysiloxane (Preparation Example 1) | q.s. |
| 10. Composite powder of hybrid silicone[2] | 1.5 |
| 11. Polymethylsilsesquioxane spherical powder[3] | 2.5 |
| 12. Antiseptics | q.s. |
| 13. Perfume | q.s. |

[1]Crosslinked alkyl-modified dimethylpolysiloxane: KSG-41 from Shin-Etsu Chemical Co., Ltd.
[2]Composite powder of hybrid silicone$^2$: KSP-100 from Shin-Etsu Chemical Co., Ltd.
[3]Polymethylsilsesquioxane spherical powder: KMP-590 from Shin-Etsu Chemical Co., Ltd.

Preparation Procedures

A: Components 5 to 12 were mixed and dispersed.

B: Components 1 to 4 were mixed and added to the dispersion prepared in the step A.

C: To the mixture prepared in the step B, Component 13 was added, which was then press-molded in a metal-mold.

The powder eye brow thus obtained was non-tacky and spread lightly on the skin to give moisturized and refreshing feel with good affinity with the skin. The applied eye brow was resistant to water and sweat and lasted long. The eye brow was found to be stable with time and temperature.

Example 25

Eye Shadow

| Components | wt % |
| --- | --- |
| 1. Sericite | 40.0 |
| 2. Mica treated with organopolysiloxane (Preparation Example 2) | 10.0 |
| 3. Talc treated with organopolysiloxane (Preparation Example 2) | Balance |
| 4. Titanium dioxide (Example 2) | 10.0 |
| 5. Titanium dioxide fine particles | 5.0 |
| 6. Magnesium stearate | 3.0 |
| 7. Pigment | q.s. |
| 8. Octyl dodecanol | 3.0 |
| 9. Dimethylpolysiloxane (6 mm$^2$/sec at 25° C.) | 4.0 |
| 10. Crosslinked dimethylpolysiloxane[1] | 6.0 |
| 11. Antiseptics | q.s. |
| 12. Perfume | q.s. |

[1]Crosslinked dimethylpolysiloxane: KSG-16 from Shin-Etsu Chemical Co., Ltd.

Preparation Procedures

A: Components 8 to 11 were mixed.

B: Components 1 to 7 were mixed, to which the mixture prepared in the step A was added.

C: To the mixture prepared in the step B, Component 12 was added.

The eye shadow thus obtained was non-tacky and spread lightly on the skin to give gloss finish which lasted long with good affinity with the skin.

Example 26

Eye Shadow

| Components | wt % |
| --- | --- |
| 1. Decamethylcyclopentasiloxane | 15.0 |
| 2. Dimethylpolysiloxane (6 mm$^2$/sec at 25° C.) | 10.0 |
| 3. Branched polyether-modified silicone[1] | 2.0 |
| 4. PEG (10)lauryl ether | 0.5 |
| 5. Chromium oxide treated with organopolysiloxane (Preparation Example 2) | 6.2 |
| 6. Ultramarine treated with organopolysiloxane (Preparation Example 2) | 4.0 |
| 7. Titanium-coated mica treated with organopolysiloxane (Preparation Example 2) | 6.0 |
| 8. Sodium chloride | 2.0 |
| 9. Propylene glycol | 8.0 |
| 10. Antiseptics | q.s. |
| 11. Perfume | q.s. |
| 12. Purified water | Balance |

[1]Branched polyether-modified silicone: KF-6028 from Shin-Etsu Chemical Co., Ltd.

Preparation Procedures

A: Components 1 to 4 were mixed, to which Components 5 to 7 were added and dispersed.

B: Components 8 to 10 and 12 were mixed and dissolved.

C: To the dispersion prepared in the step A, the solution prepared in the step B was added and emulsified, to which Component 11 was added while stirring.

The eye shadow thus obtained spread lightly on the skin to give non-greasy, non-powdery, moisturized and refreshing feel. The applied eye shadow was water-repellent and resistant to water and sweat and lasted long. It was found to be stable with time and temperature.

Example 27

Stick Eye Shadow

| Components | wt % |
| --- | --- |
| 1. Ethylene glycol distearate | 12.0 |
| 2. Crosslinked methylphenylpolysiloxane[1] | 5.0 |
| 3. Isotridecyl isononanate | 35.0 |
| 4. Candelilla wax | 1.5 |
| 5. Lecithin | 0.2 |
| 6. Composite powder of hybrid silicone[2] | 4.0 |
| 7. Iron oxide treated with organopolysiloxane (Preparation Example 2) | 6.2 |
| 8. Titanium-coated mica treated with organopolysiloxane (Preparation Example 2) | Balance |

[1]Crosslinked methylphenylpolysiloxane: KSG-18 from Shin-Etsu Chemical Co., Ltd.
[2]Composite powder of hybrid silicone: KSP-100 from Shin-Etsu Chemical Co., Ltd.

Preparation Procedures

A: Components 2 and 3 were mixed.

B: Components 1, 4 and 5 were heat-mixed, to which the mixture prepared in the step A was added and warmed.

C: Components 6 to 8 were mixed.

D: To the mixture prepared in the step B, the mixture prepared in the step C was added, which was then poured in a mold.

The stick eye shadow thus obtained spread lightly on the skin to give non-greasy and non-powdery feel. The applied eye shadow stuck well to the skin which was water-repellent, resistant to water and sweat, and lasted long with good affinity with the skin. It was found to be stable with time and temperature.

Example 28

Cream Eye Shadow

| Components | wt % |
| --- | --- |
| 1. Acrylic silicone resin[1] | 10.0 |
| 2. Acrylic silicone resin having a long-alkyl chain[2] | 2.0 |
| 3. Branched polyether-modified silicone[3] | 1.5 |
| 4. Decamethylcyclopentasiloxane | 20.3 |
| 5. Cetyl isooctanoate | 3.0 |
| 6. Bentonite modified with an organic compound | 1.2 |
| 7. Polyamide | 3.0 |
| 8. Talc treated with organopolysiloxane (Preparation Example 2) | 4.0 |
| 9. Iron oxide treated with organopolysiloxane (Preparation Example 2) | 20.0 |
| 10. Ethyl alcohol | 5.0 |
| 11. Antiseptics | q.s. |
| 12. Purified water | 30.0 |

[1]Acrylic silicone resin: KP-545 from Shin-Etsu Chemical Co., Ltd.
[2]Acrylic silicone resin having a long-alkyl chain: KP-561P from Shin-Etsu Chemical Co., Ltd.
[3]Branched polyether-modified silicone: KF-6028 from Shin-Etsu Chemical Co., Ltd.

Preparation Procedures

A: Components 1 to 6 were mixed, to which Components 7 to 9 were added and dispersed.

B: Components 10 and 12 were mixed.

C: To the dispersion prepared in the step A, the homogeneous mixture prepared in the step B was added and emulsified while stirring.

The cream eye shadow thus obtained spread lightly on the skin to give non-greasy and non-powdery feel. The applied eye shadow stuck well to the skin which was water-repellent, resistant to water and sweat, and lasted long with good affinity with the skin. It was found to be stable with time and temperature.

Example 29

Lip Stick

| Components | wt % |
|---|---|
| 1. Candelilla wax | 8.0 |
| 2. Polyethylene wax | 8.0 |
| 3. Acrylic silicone resin having a long-alkyl chain[1] | 12.0 |
| 4. Methylphenylpolysiloxane[2] | 3.0 |
| 5. Isotridecyl isononanate | 20.0 |
| 6. Glyceryl isostearate | 16.0 |
| 7. Polyglyceryl triisostearate | 28.5 |
| 8. Red No. 202 treated with organopolysiloxane (Preparation Example 2) | 0.8 |
| 9. Iron oxide red treated with organopolysiloxane (Preparation Example 2) | 1.5 |
| 10. Iron oxide yellow treated with organopolysiloxane (Preparation Example 2) | 1.0 |
| 11. Iron oxide black treated with organopolysiloxane (Preparation Example 2) | 0.2 |
| 12. Titanium dioxide (Example 2) | 1.0 |
| 13. Antiseptics | q.s. |
| 14. Perfume | q.s. |

[1] Acrylic silicone resin having a long-alkyl chain: KP-561P from Shin-Etsu Chemical Co., Ltd.
[2] Methylphenylpolysiloxane: KF-54 from Shin-Etsu Chemical Co., Ltd.

Preparation Procedures

A: Components 1 to 6 and a part of Component 7 were heat-mixed and melted.

B: Components 8 to 14 and the rest of Component 7 were mixed and added to the mixture prepared in the step A.

The lip stick thus obtained spread lightly on the lips to give non-greasy, non-powdery and refreshing feel. The applied lip stick was water-repellent and resistant. It was found to be stable.

Example 30

Liquid Lip Stick

| Components | wt % |
|---|---|
| 1. Dextrin palmitic acid/ethyl hexanoic acid ester[1] | 7.0 |
| 2. Glyceryl trioctanoate | 12.0 |
| 3. Crosslinked alkyl-modified dimethylpolysiloxane[2] | 6.0 |
| 4. Branched alkyl/polyglycerin co-modified silicone[3] | 2.0 |
| 5. Decamethylcyclopentasiloxane | 34.0 |
| 6. Dipropylene glycol | 4.0 |
| 7. Antiseptics | q.s. |
| 8. Purified water | 16.0 |
| 9. Polyglyceryl triisostearate | 5.4 |
| 10. Sericite treated with organopolysiloxane (Preparation Example 1) | 1.0 |
| 11. Red No. 201 treated with organopolysiloxane (Preparation Example 1) | 0.2 |
| 12. Red No. 202 treated with organopolysiloxane (Preparation Example 1) | 0.5 |
| 13. Yellow No. 4 aluminum lake treated with organopolysiloxane (Preparation Example 1) | 1.6 |
| 14. Iron oxide red treated with organopolysiloxane (Preparation Example 1) | 1.0 |
| 15. Iron oxide black treated with organopolysiloxane (Preparation Example 1) | 0.3 |
| 16. Titanium dioxide (Example 1) | 4.0 |
| 17. Mica | 5.0 |
| 18. Perfume | q.s. |

[1] Dextrin palmitic acid/ethyl hexanoic acid ester: Rheopearl TT frin Chiba Flour Milling Co., Ltd.
[2] Crosslinked alkyl-modified dimethylpolysiloxane: KSG-43 from Shin-Etsu Chemical Co., Ltd.
[3] Branched alkyl/polyglycerin co-modified silicone: KF-6105 from Shin-Etsu Chemical Co., Ltd.

Preparation Procedures

A: Components 1 to 5 were heat-mixed.

B: Components 6 to 8 were heat-mixed.

C: Components 10 to 16 were mixed, to which Component 9 was added.

D: The mixture prepared in the step B was added to the mixture prepared in the step A and emulsified, which was then added to the mixture prepared in the step C. To the emulsion thus obtained, Components 17 and 18 were added, which was then poured in a mold and cooled.

The liquid lip stick thus obtained spread lightly on the lips to give non-greasy, non-powdery feel and gloss finish. It was found to be stable with time and temperature.

Example 31

Lip Stick

| Components | wt % |
|---|---|
| 1. Candelilla wax | 3.5 |
| 2. Polyethylene wax | 2.0 |
| 3. Microcrystalline wax | 3.0 |
| 4. Cerisin wax | 5.5 |
| 5. Norbornene-modified silicone wax resin[1] | 13.0 |
| 6. Branched alkyl/polyglycerin-co-modified silicone[2] | 3.0 |
| 7. *Macadamia* nut oil | 20.0 |
| 8. Isostearyl malate | 8.0 |
| 9. Hydrogenated polyisobutene | 8.0 |
| 10. Isotridecyl isononanate | 15.0 |
| 11. Polyglyceryl triisostearate | 5.4 |
| 12. Sericite treated with organopolysiloxane (Preparation Example 2) | 1.0 |
| 13. Red No. 201 treated with organopolysiloxane (Preparation Example 2) | 0.2 |
| 14. Red No. 202 treated with organopolysiloxane (Preparation Example 2) | 0.5 |
| 15. Yellow No. 4 aluminum lake treated with organopolysiloxane (Preparation Example 2) | 1.6 |
| 16. Iron oxide red treated with organopolysiloxane (Preparation Example 2) | 1.0 |
| 17. Iron oxide black treated with organopolysiloxane (Preparation Example 2) | 0.3 |
| 18. Titanium dioxide (Example 2) | 4.0 |
| 19. Mica | 5.0 |
| 20. Antiseptics | q.s. |
| 21. Perfume | q.s. |

[1] Norbornene-modified silicone wax resin: KF-7020 from Shin-Etsu Chemical Co., Ltd.
[2] Branched alkyl/polyglycerin-co-modified silicone: KF-6105 from Shin-Etsu Chemical Co., Ltd.

Preparation Procedures

A: Components 1 to 10 and 20 were heat-mixed and melted.

B: Components 12 to 18 and 11 were mixed and then added to the mixture prepared in the step A.

C: To the mixture prepared in the step B, Components 19 and 21 were added and mixed, which was then poured in a mold and cooled.

The liquid lip stick thus obtained spread softly and lightly on the lips to give non-greasy and non-powdery feel. It adhered well on the lips to form gloss finish. The applied lip stick absorbs water to adhere to the lips and lasted long on the lips. The lip stick was found to be stable with time and temperature.

Example 32

Lip Stick

| Components | wt % |
|---|---|
| 1. Candelilla wax | 3.5 |
| 2. Polyethylene wax | 2.0 |
| 3. Microcrystalline wax | 3.0 |
| 4. Ceresin wax | 5.5 |
| 5. Acrylic silicone resin having a long-alkyl chain[1] | 13.0 |
| 6. Alkyl-modified crosslinked polyether-modified silicone[2] | 10.0 |
| 7. *Macadamia* nut oil | 20.0 |
| 8. Diisostearyl malate | 8.0 |
| 9. Hydrogenated polyisobutene | 12.0 |
| 10. Isotridecyl isononanate | 4.0 |
| 11. Polyglyceryl triisostearate | 5.4 |
| 12. Sericite treated with organopolysiloxane (Preparation Example 1) | 1.0 |
| 13. Red No. 201 treated with organopolysiloxane (Preparation Example 1) | 0.2 |
| 14. Red No. 202 treated with organopolysiloxane (Preparation Example 2) | 0.5 |
| 15. Yellow No. 4 aluminum lake treated with organopolysiloxane (Preparation Example 2) | 1.6 |
| 16. Iron oxide red treated with organopolysiloxane (Preparation Example 2) | 1.0 |
| 17. Iron oxide black treated with organopolysiloxane (Preparation Example 2) | 0.3 |
| 18. Titanium oxide (Example 1) | 4.0 |
| 19. Mica | 5.0 |
| 20. Antiseptics | q.s. |
| 21. Perfume | q.s. |

[1] Acrylic silicone resin having a long-alkyl chain: KP-561P from Shin-Etsu Chemical Co., Ltd.
[2] Alkyl-modified crosslinked polyether-modified silicone: KSG-330 from Shin-Etsu Chemical Co., Ltd.

Preparation Procedures

A: Components 1 to 10 and 20 were heat-mixed.

B: Components 12 to 18 and 11 were mixed and then added to the mixture prepared in the step A.

C: To the mixture prepared in the step B. Components 19 and 21 were added and mixed, which was then poured in a mold and cooled.

The liquid lip stick thus obtained spread softly and lightly on the lips to give non-greasy and non-powdery feel. It adhered well on the lips to form gloss finish. The applied lip stick abs orbs water to adhere to the lips and lasted long on the lips. The lip stick was found to be stable with time and temperature.

Example 33

Long-Lasting Lip Stick

| Components | wt % |
|---|---|
| 1. Candelilla wax | 8.0 |
| 2. Polyethylene wax | 5.0 |
| 3. Microcrystalline wax | 1.0 |
| 4. Acrylic silicone resin having a long-alkyl chain[1] | 8.0 |
| 5. *Macadamia* nut oil | 6.0 |
| 6. Diisostearyl malate | 1.0 |
| 7. Isotridecyl isononanate | 4.0 |
| 8. Acrylic silicone resin[2] | 45.0 |
| 9. Tetramethylcyclopentahexasiloxane | 3.0 |
| 10. Polyglyceryl triisostearate | 5.4 |
| 11. Sericite treated with organopolysiloxane (Preparation Example 1) | 1.0 |
| 12. Red No. 201 treated with organopolysiloxane (Preparation Example 1) | 0.2 |
| 13. Red. No. 202 treated with organopolysiloxane (Preparation Example 1) | 0.5 |
| 14. Yellow No. 4 aluminum lake treated with organopolysiloxane (Preparation Example 1) | 1.6 |
| 15. Iron oxide red treated with organopolysiloxane (Preparation Example 1) | 1.0 |
| 16. Iron oxide black treated with organopolysiloxane (Preparation Example 1) | 0.3 |
| 17. Titanium dioxide (Example 1) | 4.0 |
| 18. Mica | 5.0 |
| 19. Antiseptics | q.s. |
| 20. Perfume | q.s. |

[1] Acrylic silicone resin having a long-alkyl chain: KP-561P from Shin-Etsu Chemical Co., Ltd.
[2] Acrylic silicone resin: KP-545 from Shin-Etsu Chemical Co., Ltd.

Preparation Procedures

A: Components 1 to 7 and 19 were heat-mixed and melted.

B: Components 11 to 17 and 10 were mixed and then added to the mixture prepared in the step A.

C: To the mixture prepared in the step B, Components 8, 9 and 20 were added and mixed, which was then poured in a sealable container.

The long-lasting liquid lip stick thus obtained spread lightly on the lips to give non-greasy and non-powdery feel, and gloss finish. The applied lip stick, after volatiles evaporated, was soft and adhered well to the lips and lasted long with good water-repellency and resistance to water. The lip stick was found to be stable with time and temperature.

Example 34

Foundation

| Components | wt % |
|---|---|
| 1. Decamethylcyclopentasiloxane | 45.0 |
| 2. Dimethylpolysiloxane (6 mm$^2$/sec at 25° C.) | 5.0 |
| 3. Branched polyether-modified silicone[1] | 2.0 |
| 4. Montmorillonite modified with octadecyldimethylbenzylammonium | 4.0 |
| 5. Titanium dioxide treated with organopolysiloxane (Preparation Example 1) | 10.0 |
| 6. Talc treated with organopolysiloxane (Preparation Example 1) | 6.0 |
| 7. Mica treated with organopolysiloxane (Preparation Example 1) | 6.0 |
| 8. Iron oxide red treated with organopolysiloxane (Preparation Example 1) | 1.6 |
| 9. Iron oxide yellow treated with organopolysiloxane (Preparation Example 1) | 0.7 |

-continued

| Components | wt % |
| --- | --- |
| 10. Iron oxide black treated with organopolysiloxane (Preparation Example 1) | 0.2 |
| 11. Dipropylene glycol | 5.0 |
| 12. Methyl paraoxybenzoate | 0.3 |
| 13. 2-amino-2-methyl-1,3-propane diol | 0.2 |
| 14. Hydrochloric acid | 0.1 |
| 15. Perfume | q.s. |
| 16. Purified water | Balance |

[1]Branched polyether-modified silicone: KF-6028 from Shin-Etsu Chemical Co., Ltd.

Preparation Procedures

A: Components 1 to 4 were heat-mixed, to which Components 5 to 10 were added and mixed.

B: Components 11 to 14 and 16 were heated and dissolved (A pH of the solution was 9.0).

C: To the mixture prepared in the step A, the solution prepared in the step B was added and emulsified while stirring. The emulsion thus obtained was cooled, to which Component 15 was added.

The foundation thus obtained had fine texture. It spread lightly on the skin to give non-tacky, non-greasy, moisturized and refreshing feel. The applied foundation lasted long on the skin. The foundation was found to be stable with time and temperature.

Example 35

Powder Foundation

| Components | wt % |
| --- | --- |
| 1. Vaseline | 2.0 |
| 2. Squalane | 2.0 |
| 3. Dimethylpolysiloxane (20 mm$^2$/sec at 25° C.) | 3.0 |
| 4. Polyethylene powder | 1.5 |
| 5. Sericite treated with organopolysiloxane (Preparation Example 1) | 40.0 |
| 6. Barium sulfate | 8.5 |
| 7. Titanium dioxide (Example 2) | 9.0 |
| 8. Composite powder of phenyl-modified hybrid Silicone[1] | 3.0 |
| 9. Polymethylsilsesquioxane spherical powder[2] | 4.5 |
| 10. Talc treated with organopolysiloxane (Preparation Example 2) | 25.0 |
| 11. Iron oxide red treated with organopolysiloxane (Preparation Example 2) | 0.4 |
| 12. Iron oxide yellow treated with organopolysiloxane (Preparation Example 2) | 1.0 |
| 13. Iron oxide black treated with organopolysiloxane (Preparation Example 2) | 0.1 |
| 14. Antiseptics | q.s. |
| 15. Perfume | q.s. |

[1]Composite powder of phenyl-modified hybrid silicone: KSP-300 from Shin-Etsu Chemical Co., Ltd.
[2]Polymethylsilsesquioxane spherical powder: KMP-590 from shin-Etsu Chemical Co., Ltd.

Preparation Procedures

A: Components 1 to 3 were mixed.

B: Components 4 to 14 were mixed.

C: To the mixture prepared in the step A, the homogeneous mixture prepared in the step B and Component 15 were added, which was put in a container and pressed.

The powder foundation thus obtained spread smoothly and lightly on the skin to give silky finish to the touch without powderiness, tackiness, and greasiness. The applied foundation was resistant to water and sweat and lasted long on the skin with good affinity with the skin. The foundation was found to be stable with time and temperature.

Example 36

Liquid Emulsified Foundation

| Components | wt % |
| --- | --- |
| 1. Dimethylpolysiloxane (100 mm$^2$/sec at 25° C.) | 4.5 |
| 2. Decamethylcyclopentasiloxane | 15.0 |
| 3. Squalane | 4.0 |
| 4. Neopentyl glycol dioctanoate | 3.0 |
| 5. Myristic acid/isostearic acid diglyceride | 2.0 |
| 6. α-diisostearyl glyceryl ether | 1.0 |
| 7. Polyether-modified silicone[1] | 1.0 |
| 8. Branched alkyl/polyglycerin-co-modified silicone[2] | 0.5 |
| 9. Titanium dioxide (Example 2) | 5.0 |
| 10. Sericite treated with organopolysiloxane (Preparation Example 1) | 2.0 |
| 11. Talc treated with organopolysiloxane (Preparation Example 1) | 3.0 |
| 12. Iron oxide red treated with organopolysiloxane (Preparation Example 2) | 0.4 |
| 13. Iron oxide yellow treated with organopolysiloxane (Preparation Example 2) | 0.7 |
| 14. Iron oxide black treated with organopolysiloxane (Preparation Example 2) | 0.1 |
| 15. Magnesium sulfate | 0.7 |
| 16. Glycerin | 3.0 |
| 17. Antiseptics | q.s. |
| 18. Perfume | q.s. |
| 19. Purified water | 54.0 |

[1]Polyether-modified silicone: KF-6017 from Shin-Etsu Chemical Co., Ltd.
[2]Branched alkyl/polyglycerin-co-modified silicone: KF-6105 from Shin-Etsu Chemical Co., Ltd.

Preparation Procedures

A: Components 4 and 8 were mixed, to which Components 9 to 14 were added and dispersed.

B: Components 1 to 3, and 5 to 7 were mixed.

C: Components 15 to 17 and 19 were mixed.

D: To the mixture prepared in the step B, the mixture prepared in the step A was added, to which the mixture prepared in the step C was added and emulsified while stirring. To the emulsion thus obtained, Component 18 was added.

The liquid emulsified foundation thus obtained had a low viscosity and fine texture. It spread lightly on the skin to give non-tacky, non-greasy, moisturized and refreshing feel.

The applied foundation lasted long on the skin. The foundation was found to be stable with time and temperature.

Example 37

Liquid Foundation

| Components | wt % |
| --- | --- |
| 1. Decamethylcyclopentasiloxane | 16.0 |
| 2. Dimethylpolysiloxane (6 mm$^2$/sec at 25° C.) | 8.0 |
| 3. Octyl paramethoxycinnamate | 3.0 |
| 4. 12-hydroxystearic acid | 1.0 |
| 5. Fluorine-modified silicone[1] | 15.0 |
| 6. Fluoroalkyl/polyether-co-modified silicone[2] | 5.0 |
| 7. Polymethylsilsesquioxane spherical powder[3] | 3.0 |
| 8. Titanium oxide fine particles treated with organopolysiloxane (Preparation Exampl 1) | 8.0 |
| 9. Mica/titanium dioxide treated with organopolysiloxane (Preparation Example 1) | 1.0 |

-continued

| Components | wt % |
|---|---|
| 10. Titanium dioxide (Example 2) | 5.0 |
| 11. Silicone-treated iron oxide red[4] | 0.9 |
| 12. Silicone-treated iron oxide yellow[4] | 2.0 |
| 13. Silicone-treated iron oxide black[4] | 1.0 |
| 14. Ethyl alcohol | 15.0 |
| 15. Glycerin | 3.0 |
| 16. Magnesium sulfate | 1.0 |
| 17. Antiseptics | q.s. |
| 18. Perfume | q.s. |
| 19. Purified water | Balance |

[1] Fluorine-modified silicone: FL-50 from Shin-Etsu Chemical Co., Ltd.
[2] Fluoroalkyl/polyether-co-modified silicone: FPD-4694 from Shin-Etsu Chemical Co., Ltd.
[3] Polymethylsilsesquioxane spherical powder: KMP-590 from Shin-Etsu Chemical Co., Ltd.
[4] Silicone: KF-9909 from Shin-Etsu Chemical Co., Ltd.

Preparation Procedures

A: Components 7 and 13 were mixed.

B: Components 1 to 6 were heated at 70° C. and mixed. To the mixture obtained, the mixture prepared in the step A was added and dispersed.

C: Components 14 to 17 and 19 were heated at 40° C. The mixture thus obtained was gradually added to the homogeneous mixture prepared in the step B and emulsified. The emulsion was cooled, to which Component 18 was added.

The liquid foundation thus obtained spread lightly on the skin to give non-tacky and refreshing feel. It had ultraviolet light screening effect and was found to be stable with time and temperature.

Example 38

Oil-In-Water Type Liquid Foundation

| Components | wt % |
|---|---|
| 1. Stearci acid | 1.0 |
| 2. Behenyl alcohol | 0.4 |
| 3. Glyceryl stearate | 0.3 |
| 4. Liquid paraffin | 10.0 |
| 5. Glyceryl trioctanoate | 5.0 |
| 6. Acrylic silicone resin having a long-alkyl chain[1] | 3.0 |
| 7. Sorbitan sesquioleate | 0.5 |
| 8. Sorbitan monooleate | 1.0 |
| 9. Acryl/alkyl copolymer | 2.2 |
| 10. Triethanolamine | 1.0 |
| 11. Ethyl alcohol | 3.0 |
| 12. Composite powder of hybrid silicone[2] | 3.0 |
| 13. Polyether-modified silicone[3] | 0.2 |
| 14. Alkyl/POE palmityl ether phosphate | 0.1 |
| 15. POE hydrogenated castor oil | 0.5 |
| 16. Titanium dioxide (Example 1) | 8.5 |
| 17. Iron oxide red treated with organopolysiloxane (Preparation Example 1) | 0.4 |
| 18. Iron oxide yellow treated with organopolysiloxane (Preparation Example 1) | 1.0 |
| 19. Iron oxide black treated with organopolysiloxane (Preparation Example 1) | 0.1 |
| 20. 1,3-butylene glycol | 7.0 |
| 21. Antiseptics | q.s. |
| 22. Perfume | q.s. |
| 23. Purified water | 51.8 |

[1] Acrylic silicone resin having a long-alkyl chain: KP-561P from Shin-Etsu Chemical Co., Ltd.
[2] Composite powder of hybrid silicone: KSP-100 from Shin-Etsu Chemical Co., Ltd.
[3] Polyether-modified silicone: KF-6013 from Shin-Etsu Chemical Co., Ltd.

Preparation Procedures

A: Components 13 to 15 and a part of Component 20 were mixed, in which Components 16 to 19 were dispersed while warming.

B: Components 1 to 8 were heat-mixed.

C: Components 9, 10, the rest of Component 20, Components 21 and 23 were mixed and warmed.

D: Components 11 and 12 were mixed.

E: To the mixture prepared in the step C, the mixture prepared in the step B was added and emulsified while stirring, to which the mixture prepared in the step A, then the mixture prepared in the step D and Component 22 were added.

The oil-in-water type liquid emulsified foundation thus obtained had fine texture. It spread lightly on the skin to give non-tacky and moisturized feel. The applied foundation formed a beautiful layer which was water-repellent, and resistant to water and sweat, and lasted long. The foundation was found to be stable with time and temperature.

Example 39

Water-In-Oil Type Liquid Foundation

| Components | wt % |
|---|---|
| 1. Crosslinked polyether-modified silicone[1] | 3.5 |
| 2. Crosslinked dimethylpolysiloxane[2] | 5.0 |
| 3. Branched polyether-modified silicone[3] | 2.0 |
| 4. Bentonite modified with an organic compound | 1.2 |
| 5. Glyceryl trioctanoate | 5.0 |
| 6. Dimethylpolysiloxane (6 mm$^2$/sec at 25° C.) | 6.5 |
| 7. Decamethylcyclopentasiloxane | 13.6 |
| 8. Acryl acid-containing acrylic silicone resin[4] | 1.5 |
| 9. Titanium dioxide (Example 1) | 8.5 |
| 10. Iron oxide red treated with organopolysiloxane (Preparation Example 2) | 0.4 |
| 11. Iron oxide yellow treated with organopolysiloxane (Preparation Example 2) | 1.0 |
| 12. Iron oxide black treated with organopolysiloxane (Preparation Example 2) | 0.1 |
| 13. Dispersion of titanium dioxide fine particles[5] | 10.0 |
| 14. 1,3-butylene glycol | 5.0 |
| 15. Sodium citrate | 0.2 |
| 16. Sodium chloride | 0.5 |
| 17. Antiseptics | q.s. |
| 18. Perfume | q.s. |
| 19. Purified water | 36.0 |

[1] Crosslinked polyether-modified silicone: KSG-210 from Shin-Etsu Chemical Co., Ltd.
[2] Crosslinked dimethylpolysiloxane: KSG-15 from Shin-Etsu Chemical Co., Ltd.
[3] Branched polyether-modified silicone: KF-6028 from Shin-Etsu Chemical Co., Ltd.
[4] Acryl acid-containing acrylic silicone resin: KP-575 from Shin-Etsu Chemical Co., Ltd.
[5] Dispersion of titanium oxide fine particles: SPD-T5 from Shin-Etsu Chemical Co., Ltd.

Preparation Procedures

A: Component 8 and a part of Component 7 were mixed, to which Components 9 to 12 were added and dispersed.

B: Components 1 to 6, and the rest of Component 7 were mixed.

C: Components 14 to 17 and 19 were mixed.

D: To the mixture prepared in the step B, the mixture prepared in the step C was added and emulsified, to which the mixture prepared in the step A, and Components 13 and 18 were added while stirring.

The water-in-oil type liquid emulsified foundation thus obtained had fine texture. It spread lightly on the skin to give non-tacky and moisturized feel. The applied foundation formed a beautiful layer which was water-repellent, and resistant to water and sweat, and lasted long. The foundation was found to be stable with time and temperature.

Example 40

Water-In-Oil Type Cream Foundation

| Components | wt % |
|---|---|
| 1. Alkyl-modified crosslinked polyether-modified silicone[1] | 2.0 |
| 2. Crosslinked alkyl-modified dimethylpolysiloxane[2] | 2.0 |
| 3. Branched alkyl/polyether-comodified silicone[3] | 1.0 |
| 4. Liquid paraffin | 2.0 |
| 5. Glyceryl trioctanoate | 5.0 |
| 6. Isotridecyl isononanate | 9.0 |
| 7. Lecithin | 0.3 |
| 8. Polysolvate 80 | 0.3 |
| 9. Composite powder of hybrid silicone[4] | 2.0 |
| 10. Titanium dioxide (Example 2) | 8.5 |
| 11. Iron oxide red treated with organopolysiloxane (Preparation Example 2) | 0.4 |
| 12. Iron oxide yellow organopolysiloxane (Preparation Example 2) | 1.0 |
| 13. Iron oxide black organopolysiloxane (Preparation Example 2) | 0.1 |
| 14. 1,3-butylene glycol | 5.0 |
| 15. Sodium citrate | 0.2 |
| 16. Sodium chloride | 0.5 |
| 17. Antiseptics | q.s. |
| 18. Perfume | q.s. |
| 19. Purified water | 60.6 |

[1]Alkyl-modified crosslinked polyether-modified silicone: KSG-310 from Shin-Etsu Chemical Co., Ltd.
[2]Alkyl-modified crosslinked polyether-modified silicone: KSG-41 from Shin-Etsu Chemical Co., Ltd.
[3]Branched alkyl/polyether-comodified silicone: KF-6038 from Shin-Etsu Chemical Co., Ltd.
[4]Composite powder of hybrid silicone: KSP-100 from Shin-Etsu Chemical Co., Ltd.

Preparation Procedures

A: Components 7 to 9 and Component 15 were mixed, to which Components 10 to 14 were added. The mixture thus obtained was dispersed in a part of Component 19.

B: Components 1 to 6 were mixed.

C: Components 16 and 17, the rest of Component 19 were mixed.

D: To the mixture prepared in the step B, the mixture prepared in the step C was added and emulsified while stirring, to which the mixture prepared in the step A and Component 18 were added.

The water-in-oil type cream foundation thus obtained had fine texture. It spread lightly on the skin to give non-tacky and moisturized feel, and silky finish. The applied foundation formed a beautiful layer which was water-repellent, and resistant to water and sweat, and lasted long. The foundation was found to be stable with time and temperature.

Example 41

Water-In-Oil Type Compact Foundation

| Components | wt % |
|---|---|
| 1. Ceresin | 5.5 |
| 2. Microcrystalline wax | 1.0 |
| 3. Neopentyl glycol dioctanoate | 8.0 |
| 4. Glyceryl trioctanoate | 4.0 |
| 5. Decamethylcyclopentasiloxane | 6.0 |
| 6. Dimethylpolysiloxane (6 mm²/sec at 25° C.) | 6.0 |
| 7. Crosslinked polyether-modified silicone[1] | 4.0 |
| 8. Branched alkyl/polyether-comodified silicone[2] | 1.2 |
| 9. Sorbitan tetraisostearate | 1.0 |
| 10. Glycerin | 0.5 |
| 11. Titanium dioxide (Example 2) | 8.5 |
| 12. Iron oxide red treated with organopolysiloxane (Preparation Example 2) | 0.4 |
| 13. Iron oxide yellow organopolysiloxane (Preparation Example 2) | 1.0 |
| 14. Iron oxide black organopolysiloxane (Preparation Example 2) | 0.1 |
| 15. 1,3-butylene glycol | 5.0 |
| 16. Sodium citrate | 0.2 |
| 17. Antiseptics | q.s. |
| 18. Perfume | q.s. |
| 19. Purified water | 47.6 |

[1]Crosslinked polyether-modified silicone: KSG-210 from Shin-Etsu Chemical Co., Ltd.
[2]Branched alkyl/polyether-comodified silicone: KF-6038 from Shin-Etsu Chemical Co., Ltd.

Preparation Procedures

A: Components 9 and 10 were mixed with Component 4, to which Components 11 to 14 were dispersed and warmed.

B: Components 1 to 3, and 5 to 8 were heat-mixed.

C: Components 15 to 17 and 19 were mixed and warmed.

D: To the mixture prepared in the step B, the mixture prepared in the step A was added. To the homogeneous mixture thus obtained, the mixture prepared in the step C was added and emulsified while stirring. To the emulsion thus obtain, Component 18 was added. The mixture thus obtained was poured in a container.

The water-in-oil type compact foundation thus obtained had fine texture. It spread lightly on the skin to give non-tacky and moisturized feel, and silky finish. The applied foundation formed a beautiful layer which was water-repellent, and resistant to water and sweat, and lasted long. The foundation was found to be stable with time and temperature.

Example 42

Water-In-Oil Type Stick Foundation

| Components | wt % |
|---|---|
| 1. Ceresin | 5.5 |
| 2. Inulin stearate[1] | 2.0 |
| 3. Neopentyl glycol dioctanoate | 8.0 |
| 4. Glyceryl trioctanoate | 5.0 |
| 5. Dimethylpolysiloxane (6 mm²/sec at 25° C.) | 11.5 |
| 6. Crosslinked polyglycerin-modified silicone[2] | 4.0 |
| 7. Branched alkyl/polyglycerin-comodified silicone[3] | 1.5 |
| 8. Polymethylsilsesquioxane spherical powder[4] | 1.5 |
| 9. Lecithin | 0.2 |
| 10. POE sorbitan monooleate | 0.3 |
| 11. Titanium dioxide (Example 2) | 8.5 |
| 12. Iron oxide red treated with organopolysiloxane (Preparation Example 2) | 0.4 |
| 13. Iron oxide yellow organopolysiloxane (Preparation Example 2) | 1.0 |
| 14. Iron oxide black treated with organopolysiloxane (Preparation Example 2) | 0.1 |
| 15. Dipropylene glycol | 5.0 |
| 16. Sodium citrate | 0.2 |
| 17. Sodium chloride | 0.5 |
| 18. Antiseptics | q.s. |

-continued

| Components | wt % |
|---|---|
| 19. Perfume | q.s. |
| 20. Purified water | 44.8 |

[1] Inulin stearate: Rheopearl ISK from Chiba Flour Milling Co., Ltd.
[2] Crosslinked polyglycerin-modified silicone: KSG-710 from Shin-Etsu Chemical Co., Ltd.
[3] Branched alkyl/polyglycerin-comodified silicone: KF-6105 from Shin-Etsu Chemical Co., Ltd.
[4] Polymethylsilsesquioxane spherical powder: KMP-590 from Shin-Etsu Chemical Co., Ltd.

Preparation Procedures

A: Components 9 and 10 were mixed with Component 15, to which Components 11 to 14 were added and dispersed. The dispersion thus obtained was then added to a part of Component 20 and dispersed, and then warmed.

B: Components 1 to 8 were heat-mixed.

C: Components 16 to 18 and the rest of Component 20 were mixed and warmed.

D: To the mixture prepared in the step B, the mixture prepared in the step C was added and emulsified while stirring. To the emulsion, the mixture prepared in the step A was added, to which Component 19 was added. The mixture thus obtained was poured in a container.

The water-in-oil type stick foundation thus obtained had fine texture. It spread lightly on the skin to give non-tacky and moisturized feel, and silky finish. The applied foundation formed a beautiful layer which was water-repellent, and resistant to water and sweat, and lasted long. The foundation was found to be stable with time and temperature.

Example 43

Foundation

| Components | wt % |
|---|---|
| 1. Decamethylcyclopentasiloxane | 27.0 |
| 2. Methylphenylpolysiloxane | 3.0 |
| 3. Glyceryl trioctanoate | 10.0 |
| 4. Branched alkyl/polyether-comodified silicone[1] | 1.0 |
| 5. Polyglyceryl monoisostearate | 3.0 |
| 6. Mixture of hydrophobic powder[2] | 18.0 |
| 7. Iron oxide red | 1.2 |
| 8. Iron oxide yellow | 2.6 |
| 9. Iron oxide black | 0.2 |
| 10. 1,3-butylene glycol | 7.0 |
| 11. Sodium chloride | 0.5 |
| 12. Antiseptics | q.s. |
| 13. Perfume | q.s. |
| 14. Purified water | Balance |

[1] Branched alkyl/polyether-comodified silicone: KF-6038 from Shin-Etsu Chemical Co., Ltd.
[2] Mixture of hydrophobic powder of which composition is shown below:

| a. Titanium oxide fine particles | 8.0 |
|---|---|
| b. Zinc oxide fine particles | 4.0 |
| c. Talc | 3.0 |
| d. Mica | 3.0 |

Preparation Procedures

A: The powders of a to d were mixed, to which 1 wt W of the organopolysiloxane prepared in Preparation Example 1 was added and baked.

B: Components 1 to 5 were heat-mixed to melt, in which Components 6 to 9 were dispersed homogeneously.

C: Components 10 to 12 and 14 were mixed, which was then added to the dispersion prepared in the step B and emulsified.

D: The mixture prepared in the step C was cooled, to which Component 13 was added.

The foundation thus obtained was non-tacky and spread lightly on the skin. It adhered to the skin and gave gloss finish with good affinity with the skin. The applied foundation lasted long on the skin. The foundation was found to be stable with time and temperature.

Example 44

Spray for Brushing

| Components | wt % |
|---|---|
| 1. Isopropyl myristate | 1.0 |
| 2. Stearyltrimethylammonium chloride | 0.1 |
| 3. Zinc oxide fine particles treated with organopolysiloxane (Preparation Example 1) | 3.0 |
| 4. Ethyl alcohol | 25.0 |
| 5. Perfume | q.s. |
| 6. Propellant | Balance |

Preparation Procedures

A: Components 1 and 5 were mixed.

B: The mixture prepared in the step A was put in an aerosol can, to which Component 6 was added.

The brushing spray thus obtained provided the hair with gloss finish, smoothness and easiness to comb, which effects lasted long. At the time of use, the powders were well dispersed in the spray.

Example 45

Rinse

| Components | wt % |
|---|---|
| 1. Ethylene glycol distearate | 3.0 |
| 2. Cetyl alcohol | 2.0 |
| 3. Propylene glycol monostearate | 3.0 |
| 4. Dimethylpolysiloxane (100 mm$^2$/sec at 25° C.) | 3.0 |
| 5. Glycerin monostearate | 4.0 |
| 6. Polyoxyethylene(3) stearate | 4.0 |
| 7. Acetyltrimethylammonium chloride | 5.0 |
| 8. Polyoxyethylene(20) cetyl ether | 2.0 |
| 9. Zinc oxide(Example 3) | 2.0 |
| 10. 1,3-butylene glycol | 5.0 |
| 11. Antiseptics | q.s. |
| 12. Perfume | q.s. |
| 13. Purified water | Balance |

Preparation Procedures

A: Components 1 to 8 were heat-mixed, to which Component 9 was added.

B: Components 10, 11 and 13 were mixed and heated.

C: To the mixture prepared in the step A, the mixture prepared in the step B was added and mixed. The mixture thus obtained was cooled, to which Component 12 was added.

The rinse thus obtained was not tacky and thick at the time of use. It provided the hair with gloss and silky finish, smoothness, firmness, and easiness to comb, which effects lasted long.

Example 46

Conditioning Shampoo

| Components | wt % |
| --- | --- |
| 1. Lauramidopropyldimethylamino acetate betaine (39%) | 15.0 |
| 2. Polyoxyethylene (3) lauryl ether sodium sulfate(27%) | 4.0 |
| 3. Polyoxyethylene (150) distearate | 0.5 |
| 4. Cationized cellulose(4%) | 0.5 |
| 5. Glycerin | 3.0 |
| 6. Dimethylpolysiloxane (1000,000 mm$^2$/sec at 25° C.) | 1.0 |
| 7. Dimethylpolysiloxane (100 mm$^2$/sec at 25° C.) | 3.0 |
| 8. Mica treated with organopolysiloxane (Preparation Example 1) | 2.0 |
| 9. Antiseptics | q.s. |
| 10. Perfume | q.s. |
| 11. Purified water | 71.0 |

Preparation Procedures

A: Components 1 to 5, 9 and 11 were mixed and heated.

B: Components 6 to 8 were mixed and dispersed.

C: To the mixture prepared in the step A, the dispersion prepared in the step B was added and mixed. The mixture thus obtained was cooled, to which Component 10 was added.

The conditioning shampoo thus obtained was not tacky and thick at the time of use. It provided the hair with gloss and silky finish, smoothness, firmness, and easiness to comb, which effects lasted long.

Example 47

Hair Treatment

| Components | wt % |
| --- | --- |
| 1. Ethylene glycol distearate | 1.0 |
| 2. Liquid paraffin | 10.0 |
| 3. Squalane | 5.0 |
| 4. Stearyl alcohol | 1.5 |
| 5. Dimethylpolysiloxane (10 mm$^2$/sec at 25° C.) | 3.0 |
| 6. Stearic acid | 6.0 |
| 7. Polyoxyethylene (3) stearyl alcohol | 4.5 |
| 8. Polyoxyethylene (150) cetyl alcohol | 2.0 |
| 9. Sericite treated with organopolysiloxane (Preparation Example 2) | 1.5 |
| 10. 1,3-butylene glycol | 6.0 |
| 11. Antiseptics | q.s. |
| 12. Perfume | q.s. |
| 13. Purified water | 59.5 |

Preparation Procedures

A: Components 1 to 8 were heat-mixed, to which Component 9 was added.

B: Components 10, 11 and 13 were mixed and dispersed.

C: To the homogeneous mixture prepared in the step A, the dispersion prepared in the step B was added and mixed. The mixture thus obtained was cooled, to which Component 12 was added.

The treatment thus obtained was not tacky and thick at the time of use. It provided the hair with gloss and silky finish, smoothness, firmness, and easiness to comb, which effects lasted long.

Example 48

Water-In-Oil Type Antiperspirant

| Components | wt % |
| --- | --- |
| 1. Crosslinked polyether-modified silicone[1] | 7.0 |
| 2. Decamethylcyclopentasiloxane | 10.0 |
| 3. Glyceryl trioctanoate | 7.0 |
| 4. Dipropylene glycol | 5.0 |
| 5. Sodium citrate | 0.2 |
| 6. Aluminum zirconium tetrachlorohydrate | 18.0 |
| 7. Zinc oxide treated with organopolysiloxane (Example 4) | 5.0 |
| 8. Composite powder of phenyl-modified hybrid silicone[2] | 2.0 |
| 9. Perfume | q.s. |
| 10. Purified water | 45.8 |

[1]Crosslinked polyether-modified silicone: KSG-210 from Shin-Etsu Chemical Co., Ltd.
[2]Composite powder of phenyl-modified hybrid silicone: KSP-300 from Shin-Etsu Chemical Co., Ltd.

Preparation Procedures

A: Components 1 to 3 were mixed.

B: Components 4 to 10 were mixed.

C: To the mixture prepared in the step A, the mixture prepared in the step B was added and emulsified.

The water-in-oil type antiperspirant thus obtained spread lightly to give refreshing feel without tackiness and greasiness. It was found to be stable with time and temperature.

Example 49

Roll-on Type Antiperspirant

| Components | wt % |
| --- | --- |
| 1. Crosslinked polyether-modified silicone[1] | 20.0 |
| 2. Crosslinked dimethylpolysiloxane[2] | 15.0 |
| 3. Dimethylpolysiloxane (6 mm$^2$/sec at 25° C.) | 10.0 |
| 4. Decamethylcyclopentasiloxane | 30.0 |
| 5. Aluminum zirconium tetrachlorohydrate | 20.0 |
| 6. Zinc oxide (Example 3) | 5.0 |
| 7. Perfume | q.s. |

[1]Crosslinked polyether-modified silicone: KSG-210 from Shin-Etsu Chemical Co., Ltd.
[2]Crosslinked dimethylpolysiloxane: KSG-15 from Shin-Etsu Chemical Co., Ltd.

Preparation Procedures

A: Components 1 to 4 were mixed.

B: To the mixture prepared in the step A, Components 5 to 7 were added and dispersed.

The Roll-on type antiperspirant thus obtained spread lightly to give refreshing feel without tackiness and greasiness. It was found to be stable with time and temperature.

Example 50

Sunscreen Milky Lotion

| Components | wt % |
| --- | --- |
| 1. Decamethylcyclopentasiloxane | 20.0 |
| 2. Methylphenylpolysiloxane | 3.0 |
| 3. Sorbitan monoisostearate | 1.0 |

-continued

| Components | wt % |
|---|---|
| 4. Polyether-modified silicone[1] | 1.5 |
| 5. Trimethylsiloxysilicate[2] | 1.0 |
| 6. Octyl paramethoxycinnamate | 4.0 |
| 7. Titanium dioxide fine particles treated with organopolysiloxane (Preparation Example 1) | 8.0 |
| 8. Sorbitol | 2.0 |
| 9. Sodium chloride | 2.0 |
| 10. Antiseptics | q.s. |
| 11. Perfume | q.s. |
| 12. Purified water | Balance |

[1]Polyether-modified silicone: KF-6015 from Shin-Etsu Chemical Co., Ltd.
[2]Trimethylsiloxysilicate: X-21-5250 from Shin-Etsu Chemical Co., Ltd.

Preparation Procedures

A: Components 1 to 6 were heat-mixed, in which Component 7 was dispersed.

B: Components 8 to 10 and 12 were heat-mixed.

C: To the dispersion prepared in the step A, the mixture prepared in the step B was gradually added and emulsified. The emulsion was cooled, to which Component 11 was added.

The sunscreen milky lotion thus obtained had fine texture. It spread lightly on the skin to give moisturized feel. The applied lotion was non-tacky which lasted long, maintaining ultraviolet light protective effect. It was found to be stable with time and temperature.

Example 51

Water-In-Oil Type Sunscreen Cream

| Components | wt % |
|---|---|
| 1. Crosslinked polyether-modified silicone[1] | 3.0 |
| 2. Crosslinked dimethylpolysiloxane[2] | 6.0 |
| 3. Branched alkyl/polyether-comodified silicone[3] | 1.0 |
| 4. Neopentyl glycol dioctanoate | 9.0 |
| 5. Octyl paramethoxycinnamate | 5.0 |
| 6. Dispersion of titanium dioxide fine particles[4] | 5.0 |
| 7. Zinc oxide (Example 3) | 18.0 |
| 8. Crosslinked alkyl/polyglycerin-modified silicone[5] | 1.5 |
| 9. Decamethylcyclopentasiloxane | 10.5 |
| 10. Acrylic silicone resin[6] | 12.0 |
| 11. Silica | 0.2 |
| 12. Pentylene glycol | 7.0 |
| 13. Sodium citrate | 0.2 |
| 14. Sodium chloride | 0.5 |
| 15. Perfume | q.s. |
| 16. Purified water | 21.1 |

[1]Crosslinked polyether-modified silicone: KSG-240 from Shin-Etsu Chemical Co., Ltd.
[2]Crosslinked dimethylpolysiloxane: KSG-15 from Shin-Etsu Chemical Co., Ltd.
[3]Branched alkyl/polyether-comodified silicone: KF-6038 from Shin-Etsu Chemical Co., Ltd.
[4]Dispersion of titanium oxide fine particles SPD-T5 from Shin-Etsu Chemical Co., Ltd.
[5]Crosslinked alkyl/polyglycerin-modified silicone: KF-6105 from Shin-Etsu Chemical Co., Ltd.
[6]Acrylic silicone resin: KP-545 from Shin-Etsu Chemical Co., Ltd.

Preparation Procedures

A: Components 8 and 9 were mixed, in which Component 7 was dispersed with a bead mill.

B: Components 1 to 5, 10 and 11 were mixed.

C: Components 12 to 14 and 16 were mixed.

D: To the mixture prepared in the step B, the dispersion prepared in the step A and Component 6 were added. To the homogeneous mixture thus obtained, the mixture prepared in the step C was added and emulsified. To the emulsion thus obtained, Component 15 was added.

The sunscreen cream thus obtained was non-tacky and spread lightly on the skin to give gloss finish without whitening the skin. The applied cream lasted long with good affinity with the skin, maintaining ultraviolet light protective effect. It was found to be stable with time and temperature.

Example 52

Oil-In-Water Type Sunscreen Cream

| Components | wt % |
|---|---|
| 1. Crosslinked methylphenylpolysiloxane[1] | 5.0 |
| 2. Cetyl isooctanoate | 7.0 |
| 3. Titanium dioxide fine particles[2] | 6.0 |
| 4. Decamethylcyclopentasiloxane | 8.0 |
| 5. Branched polyether-modified silicone[3] | 1.0 |
| 6. Polyether-modified silicone[4] | 1.0 |
| 7. Polyacrylamide mixture[5] | 2.0 |
| 8. Propylene glycol | 5.0 |
| 9. Methylcellulose(2% aqueous solution)[6] | 5.0 |
| 10. Antiseptics | q.s. |
| 11. Perfume | q.s. |
| 12. Purified water | 60.0 |

[1]Crosslinked methylphenylpolysiloxane KSG-18A from Shin-Etsu Chemical Co., Ltd.
[2]In a reactor, 95 parts of titanium dioxide fine particles were placed, to which a solution of 3 parts of the organopolysiloxane prepared in Preparation Example 1 and 2 parts of the organopolysiloxane prepared in Preparation Example 2 diluted in toluene was gradually added while stirring. Then, toluene was distilled off and the titanium dioxide fine particles were heated at 150° C. for 3 hours.
[3]Branched polyether-modified silicone: KF-6028 from Shin-Etsu Chemical Co., Ltd.
[4]Polyether-modified silicone: KF-6011 from Shin-Etsu Chemical Co., Ltd.
[5]Polyacrylamide mixture: Sepigel 305 from Seppic. Co.
[6]Methylcellulose: Metholose SM-4000 from Seppic. Co.

Preparation Procedures

A: Components 3 to 5 were mixed.

B: Components 1 and 2 were mixed, to which the mixture prepared in the step A was added.

C: Components 6 to 10 and 12 were mixed.

D: To the mixture prepared in the step C, the mixture prepared in the step B was added and emulsified, to which Component 11 was added.

The oil-in-water type sunscreen cream thus obtained spread lightly on the skin to give non-tacky, non-greasy and refreshing feel. The applied cream was translucent and lasted long, maintaining ultraviolet light protective effect. It was found to be stable with time and temperature.

Example 53

Sunscreen Cream

| Components | wt % |
|---|---|
| 1. Decamethylcyclopentasiloxane | 17.5 |
| 2. Acrylic silicone resin[1] | 12.0 |
| 3. Glyceryl trioctanoate | 5.0 |
| 4. Octyl paramethoxycinnamate | 6.0 |
| 5. Crosslinked polyether-modified silicone[2] | 5.0 |
| 6. Alkyl/polyether-comodified silicone[3] | 1.0 |
| 7. Zinc oxide(Example 4) | 20.0 |
| 8. Sodium chloride | 0.5 |
| 9. 1,3-butylene glycol | 2.0 |
| 10. Antiseptics | q.s. |
| 11. Perfume | q.s. |
| 12. Purified water | Balance |

[1]Acrylic silicone resin: KP-575 from Shin-Etsu Chemical Co., Ltd.
[2]Crosslinked polyether-modified silicone: KSG-210 from Shin-Etsu Chemical Co., Ltd.
[3]Alkyl/polyether-comodified silicone: KF-6026 from Shin-Etsu Chemical Co., Ltd.

Preparation Procedures

A: A part of Component 1 and Component 2 were mixed, to which Component 7 was added and dispersed with a bead mill.

B: The rest of Component 1, and Components 3 to 6 were mixed.

C: Components 8 to 10 were dissolved in Component 12.

D: To the mixture prepared in the step B, the solution prepared in the step C was added and emulsified, to which the mixture prepared in the step A and Component 11 were added.

The sunscreen cream thus obtained was non-tacky and spread lightly on the skin. It gave gloss finish which lasted long with good affinity with the skin. The cream was found to be stable with time and temperature.

Example 54

Non-Aqueous Emulsion

| Components | wt % |
|---|---|
| 1. Crosslinked dimethylpolysiloxane[1] | 30.0 |
| 2. Decamethylcyclopentasiloxane | 15.0 |
| 3. Dimethylpolysiloxane (6 mm$^2$/sec at 25° C.) | 6.0 |
| 4. Crosslinked polyglycerin-modified silicone[2] | 3.0 |
| 5. Crosslinked alkyl/polyglycerin-modified silicone[3] | 1.0 |
| 6. Dimethyldistearylammonium hectorite | 2.0 |
| 7. 1,3-butylene glycol | 38.0 |
| 8. Sorbitan tetraisostearate | 1.0 |
| 9. Titanium-coated mica treated with organopolysiloxane (Preparation Example 1) | 2.0 |

[1]Crosslinked dimethylpolysiloxane: KSG-15 from Shin-Etsu Chemical Co., Ltd.
[2]Crosslinked polyglycerin-modified silicone: KSG-710 from Shin-Etsu Chemical Co., Ltd.
[3]Crosslinked alkyl/polyglycerin-modified silicone: KF-6105 from Shin-Etsu Chemical Co., Ltd.

Preparation Procedures

A: Components 1 to 6 were mixed.

B: Components 7 to 9 were mixed.

C: To the mixture prepared in the step A, the mixture prepared in the step B was added and emulsified.

The non-aqueous emulsion thus obtained spread lightly on the skin to give non-tacky, non-greasy, and fatted feel. It was found to be stable with time and temperature.

Example 55

W/O/W Type Cream

| Components | wt % |
|---|---|
| 1. Crosslinked polyether-modified silicone[1] | 5.0 |
| 2. Cetyl isooctanoate | 5.0 |
| 3. Crosslinked alkyl-modified dimethylpolysiloxane[2] | 1.0 |
| 4. Methyl trimethicone[3] | 5.0 |
| 5. Methyl glucoside dioleate | 1.5 |
| 6. Isohexadecane | 3.5 |
| 7. Magnesium sulfate | 0.5 |
| 8. Propylene glycol | 5.0 |
| 9. Purified water | 39.5 |
| 10. Cetyl alcohol | 1.0 |
| 11. PEG-10 soya seterol | 2.0 |
| 12. Titanium-coated mica treated with organopolysiloxane (Preparation Example 1) | 0.5 |
| 13. Antiseptics | q.s. |
| 14. Perfume | q.s. |
| 15. Purified water | 30.5 |

[1]Crosslinked polyether-modified silicone: KSG-210 from Shin-Etsu Chemical Co., Ltd.
[2]Crosslinked alkyl-modified dimethylpolysiloxane: KSG-43 from Shin-Etsu Chemical Co., Ltd.
[3]Methyl trimethicone: TMF-1.5 from Shin-Etsu Chemical Co., Ltd.

Preparation Procedures

A: Components 7 to 9 were mixed.

B: Components 1 to 6 were mixed, to which the mixture prepared in the step A was added and emulsified.

C: Components 10 to 13 and 15 were heat-mixed, to which emulsion prepared in the step B was added and emulsified while stirring.

D: To the emulsion prepared in the step C, Component 14 was added.

The W/O/W type cream thus obtained spread lightly on the skin to give non-tacky, non-greasy and refreshing feel, and durable translucent finish. It was found to be stable with time and temperature.

Example 56

O/W/O Type Milky Lotion

| Components | wt % |
|---|---|
| 1. Crosslinked polyether-modified silicone[1] | 3.0 |
| 2. Glyceryl triisooctanoate | 15.0 |
| 3. Crosslinked dimethylpolysiloxane[2] | 5.0 |
| 4. Sugar monostearate | 3.0 |
| 5. Glycerin | 5.0 |
| 6. 1,3-butylene glycol | 5.0 |
| 7. Sericite treated with organopolysiloxane (Preparation Example 2) | 0.5 |
| 8. Antiseptics | q.s. |
| 9. Purified water | 60.0 |
| 10. Macadamia nut oil | 2.0 |
| 11. Cetyl alcohol | 2.0 |
| 12. Perfume | q.s. |

[1]Crosslinked polyether-modified: KSG-210 from Shin-Etsu Chemical Co., Ltd.
[2]Crosslinked dimethylpolysiloxane: KSG-15 from Shin-Etsu Chemical Co., Ltd.

Preparation Procedures

A: Components 1 to 3 were mixed.

B: Components 4 to 9 were heat-mixed.

C: Components 10 and 11 were heat-mixed.

D: To the mixture prepared in the step B, the mixture prepared in the step C was added and emulsified while stirring. The emulsion thus obtained was cooled.

E: To the mixture prepared in the step A, the emulsion prepared in the step D was added and emulsified.

The O/W/o type milky lotion thus obtained spread lightly on the skin to give non-tacky, non-greasy and refreshing feel, and durable translucent finish. It was found to be stable with time and temperature.

Example 57

O/W/O Type Liquid Foundation

| Components | wt % |
|---|---|
| 1. Alkyl-modified crosslinked polyether-modified silicone[1] | 5.0 |
| 2. Propylene glycol decanoate | 5.0 |
| 3. Isopropyl myristate | 5.0 |

-continued

| Components | wt % |
|---|---|
| 4. Titanium dioxide(Example 2) | 8.5 |
| 5. Alkylsilyl-modified iron oxide[2] | 1.5 |
| 6. Hydrogenated egg yolk-origin phospholipids | 1.0 |
| 7. Glycerin | 2.0 |
| 8. 1,3-butylene glycol | 10.0 |
| 9. Antiseptics | q.s. |
| 10. Purified water | 52.0 |
| 11. Squalane | 3.0 |
| 12. Crosslinked alkyl-modified dimethylpolysiloxane[3] | 2.0 |
| 13. Cetyl alcohol | 5.0 |
| 14. Perfume | q.s. |

[1] Alkyl-modified crosslinked polyether-modified silicone: KSG-310 from Shin-Etsu Chemical Co., Ltd.
[2] Alkylsilyl-modified iron oxide: Iron oxide treated with AES-3083 from Shin-Etsu Chemical Co., Ltd.
[3] Crosslinked alkyl-modified dimethylpolysiloxane: KSG-44 from Shin-Etsu Chemical Co., Ltd.

Preparation Procedures

A: Components 1 to 3 were mixed.

B: Components 4 to 10 were heat-mixed.

C: Components 11 to 13 were heat-mixed.

D: To the mixture prepared in the step B, the mixture prepared in the step C was added and emulsified while stirring. The emulsion thus obtained was cooled.

E: To the mixture prepared in the step A, the emulsion prepared in the step D was added and emulsified, to which Component 14 was added.

The O/W/O type liquid foundation thus obtained spread lightly on the skin to give non-tacky, non-greasy and refreshing feel, and durable translucent finish. It was found to be stable with time and temperature.

INDUSTRIAL APPLICABILITY

The surface-treated powder of the present invention is excellent in water resistance and dispersivity in unctuous agents. It is suitably used for cosmetics.

What is claimed is:

1. A powder surface-treated with an organopolysiloxane represented by the following formula:

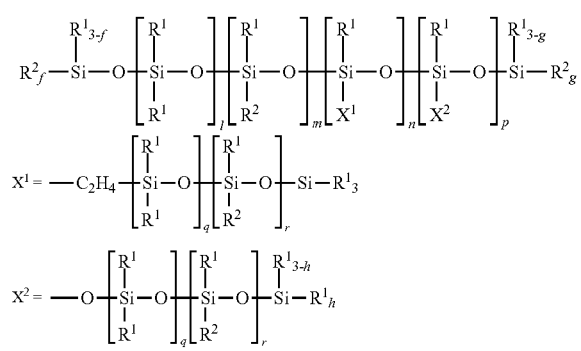

wherein
  $R^1$ is selected from the group consisting of C1-30 alkyl, C1-30 fluoroalkyl, C6-30 aryl, and C6-30 aralkyl groups,
  $R^2$ is a group represented by the following formula (2),

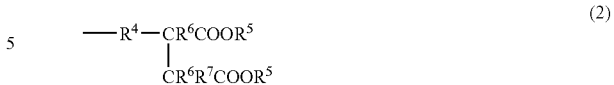

wherein $R^4$ is a C2-20 divalent hydrocarbon group which has an oxygen atom or no oxygen atom, each $R^5$ is, independently, a hydrogen atom, a monovalent cation, or a C1-10 alkyl group, provided that at least one of $R^5$'s is a hydrogen atom or a monovalent cation, each $R^6$ is, independently, a hydrogen atom or a C1-6 alkyl group, and $R^7$ is a hydrogen atom or a C1-6 alkyl group,
  l is an integer of from 0 to 500,
  m is an integer of from 2 to 50,
  n is an integer of from 1 to 10,
  p is 0,
  q is an integer of from 0 to 500,
  r is an integer of from 0 to 50, and
  f, g, and h are 0 or 1,
provided that f+g+h is at least 1, 5≤l+m≤550 and q+r ranges from 1 to 100.

2. The powder according to claim 1, wherein each $R^5$ is, independently, a hydrogen atom, a sodium ion or a potassium ion.

3. The powder according to claim 1, wherein $R^6$ and $R^7$ are hydrogen atoms.

4. The powder according to claim 1, wherein the powder is composed of an inorganic substance selected from the group consisting of zinc oxide, titanium dioxide, mica, sericite, talc, and kaolin.

5. A powder dispersion, comprising an unctuous agent and a powder surface-treated with an organopolysiloxane represented by the following formula:

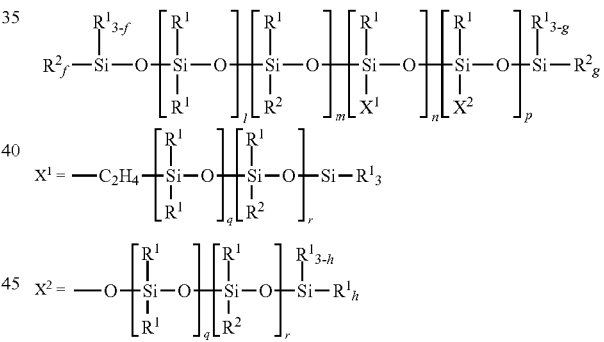

wherein
  $R^1$ is selected from the group consisting of C1-30 alkyl, C1-30 fluoroalkyl, C6-30 aryl, and C6-30 aralkyl groups,
  $R^2$ is a group represented by the following formula (2),

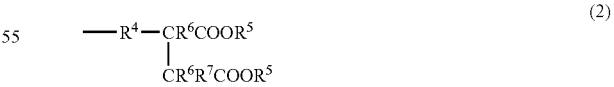

wherein $R^4$ is a C2-20 divalent hydrocarbon group which has an oxygen atom or no oxygen atom, each $R^5$ is, independently, a hydrogen atom, a monovalent cation, or a C1-10 alkyl group, provided that at least one of $R^5$'s is a hydrogen atom or a monovalent cation, each $R^6$ is, independently, a hydrogen atom or a C1-6 alkyl group, and $R^7$ is a hydrogen atom or a C1-6 alkyl group,
  l is an integer of from 0 to 500,
  m is an integer of from 2 to 50,
  n is an integer of from 1 to 10, p is 0, q is an integer of from 0 to 500, r is an integer of from 0 to 50, and f, g, and h are 0 or 1, provided that f+g+h is at least 1, $5 \leq l+m<550$ and q+r ranges from 1 to 100.

6. The powder dispersion according to claim 5, wherein the powder dispersion comprises 5 to 70 parts by weight of the powder and 30 to 95 parts by weight of the unctuous agent.

7. The powder dispersion according to claim 5, wherein the unctuous agent is at least one member selected from the group consisting of isododecane, isohexadecane, isocetyl isostearate, cetyl octanoate, and isononyl isononanate.

8. The powder dispersion according to claim 5, wherein the unctuous agent is at least one member selected from the group consisting of octamethylcyclotetrasiloxane, decamethylcyclopentasiloxane, dodecamethylcyclohexasiloxane, tetramethyltetrahydrogencyclotetrasiloxane, and tetramethyltetraphenylcyclotetrasiloxane.

9. A cosmetic, comprising a surface-treated with an organopolysiloxane represented by the following formula:

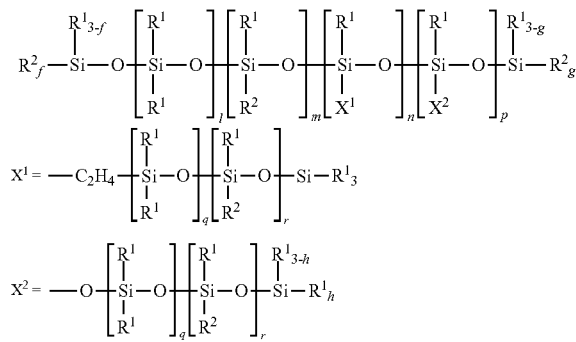

wherein $R^1$ is selected from the group consisting of C1-30 alkyl, C1-30 fluoroalkyl, C6-30 aryl, and C6-30 aralkyl groups, $R^2$ is a group represented by the following formula (2),

wherein $R^4$ is a C2-20 divalent hydrocarbon group which has an oxygen atom or no oxygen atom, each $R^5$ is, independently, a hydrogen atom, a monovalent cation, or a C1-10 alkyl group, provided that at least one of $R^5$'s is a hydrogen atom or a monovalent cation, each $R^6$ is, independently, a hydrogen atom or a C1-6 alkyl group, and $R^7$ is a hydrogen atom or a C1-6 alkyl group, l is an integer of from 0 to 500, m is an integer of from 2 to 50, n is an integer of from 1 to 10, p is 0, q is an integer of from 0 to 500, r is an integer of from 0 to 50, and f, g, and h are 0 or 1, provided that f+g+h is at least 1, $5 \leq l+m<550$ and q+r ranges from 1 to 100.

10. A powder dispersion for use in a cosmetic, comprising the powder dispersion according to claim 5.

11. The powder according to claim 1, wherein m=2.

12. The powder dispersion according to claim 5, wherein m=2.

13. The cosmetic according to claim 9, wherein m=2.

\* \* \* \* \*